(12) United States Patent
Charters et al.

(10) Patent No.: US 11,948,700 B2
(45) Date of Patent: Apr. 2, 2024

(54) IN-SITU METHOD OF DRILLING TO COLLECT DRY SAMPLES FROM A NUCLEAR REACTOR CORE INTERIOR FOR ANALYSIS

(71) Applicants: Grant Charters, Golden, CO (US); Sudesh Aggarwal, Golden, CO (US)

(72) Inventors: Grant Charters, Golden, CO (US); Sudesh Aggarwal, Golden, CO (US)

(*) Notice: Subject to any disclaimer, the term of this patent is extended or adjusted under 35 U.S.C. 154(b) by 634 days.

(21) Appl. No.: 17/094,850

(22) Filed: Nov. 11, 2020

(65) Prior Publication Data
US 2022/0148746 A1    May 12, 2022

(51) Int. Cl.
| G21C 19/20 | (2006.01) |
| G01N 1/08 | (2006.01) |
| G01T 7/02 | (2006.01) |
| G21D 1/00 | (2006.01) |
| G01N 33/20 | (2019.01) |

(Continued)

(52) U.S. Cl.
CPC .............. *G21C 19/20* (2013.01); *G01N 1/08* (2013.01); *G01T 7/02* (2013.01); *G21D 1/003* (2013.01); *G01N 33/20* (2013.01); *G21C 17/06* (2013.01); *G21C 19/02* (2013.01)

(58) Field of Classification Search
CPC . G01T 7/02; G01N 1/08; G01N 33/20; G21C 19/20; G21C 19/02; G21C 17/06; G21D 1/003
USPC ......................................................... 376/260
See application file for complete search history.

(56) References Cited

U.S. PATENT DOCUMENTS

| 4,437,333 A | 3/1984 | Hands |
| 4,483,205 A | 11/1984 | Bellaiche et al. |
| 4,616,515 A | 10/1986 | Dancoine |

(Continued)

FOREIGN PATENT DOCUMENTS

| EP | 315277 | 5/1989 |
| JP | 62222141 | 9/1987 |
| JP | 2002055031 | 2/2002 |

OTHER PUBLICATIONS

Taylor, "A Multi-Phased Sampling Effort to Characterize a University TRIGA Research Reactor", Proceedings of the WM 6, Tucson AZ (2006). (Year: 2006).*

(Continued)

*Primary Examiner* — Jack W Keith
*Assistant Examiner* — Daniel Wasil
(74) *Attorney, Agent, or Firm* — Grant Charters; Sudesh Aggarwal

(57) ABSTRACT

A method for collection of dry samples taken directly from a nuclear reactor core interior. Incremental samples of irradiated metal alloy components of the reactor core may be taken and collected in-situ using a specialized metal-cutting drill bit having a hollow tungsten carbide sampling cutting head, in conjunction with an angled sampling gantry. The drill bit body has an interior airflow passage in hermetic communication with a filter located in a glove box. Air holes are formed through a face of the cutting head. A vacuumed airflow through the airflow passage and at the cutting head causes a sample of any of metal chips, filings, and dust to be obtained directly from the reactor core by being pulled through the air holes and into the airflow passage and ultimately into the filter. A collected sample may be analyzed for radionuclides and radioactivity level.

20 Claims, 19 Drawing Sheets

(51) Int. Cl.
*G21C 17/06* (2006.01)
*G21C 19/02* (2006.01)

(56) References Cited

U.S. PATENT DOCUMENTS

| | | |
|---|---|---|
| 4,754,655 A | 7/1988 | Parker et al. |
| 4,936,153 A | 6/1990 | Klit |
| 5,553,682 A | 9/1996 | Batliner et al. |
| 5,678,960 A | 10/1997 | Just et al. |
| 5,800,101 A | 9/1998 | Jindai et al. |
| 5,939,330 A | 8/1999 | Peterson |
| 5,946,639 A | 8/1999 | Hess |
| 6,007,276 A | 12/1999 | Wardell |
| 6,032,749 A | 3/2000 | Bongers-Ambrosius et al. |
| 6,158,509 A | 12/2000 | Peterson |
| 6,289,714 B1 | 10/2001 | Tartre |
| 6,446,514 B1 | 9/2002 | Danylewych-May et al. |
| 6,466,637 B2 | 10/2002 | Bowen et al. |
| 6,966,236 B2 * | 11/2005 | Charters .......... G01N 1/08 73/866 |
| 7,070,010 B2 | 7/2006 | Papousek |
| 7,563,060 B2 | 7/2009 | Kesterson et al. |
| 7,686,105 B2 | 3/2010 | Hata |
| 8,197,162 B2 | 6/2012 | Sim et al. |

OTHER PUBLICATIONS

Booth, "Postmortem on Three Mile Island", Science 238, No. 4832 (1987): 1342-1345. (Year: 1987).*
Charters, "Material Sample Collection with Tritium and Gamma Analyses at the University of Illinois's Nuclear Research Laboratory TRIGA Nuclear Research Reactor", Waste Management (2006). (Year: 2006).*

* cited by examiner

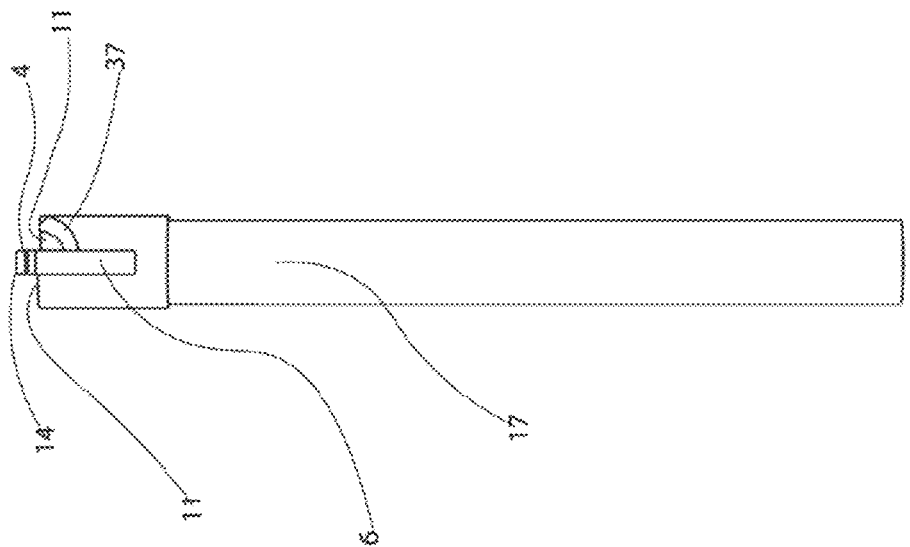

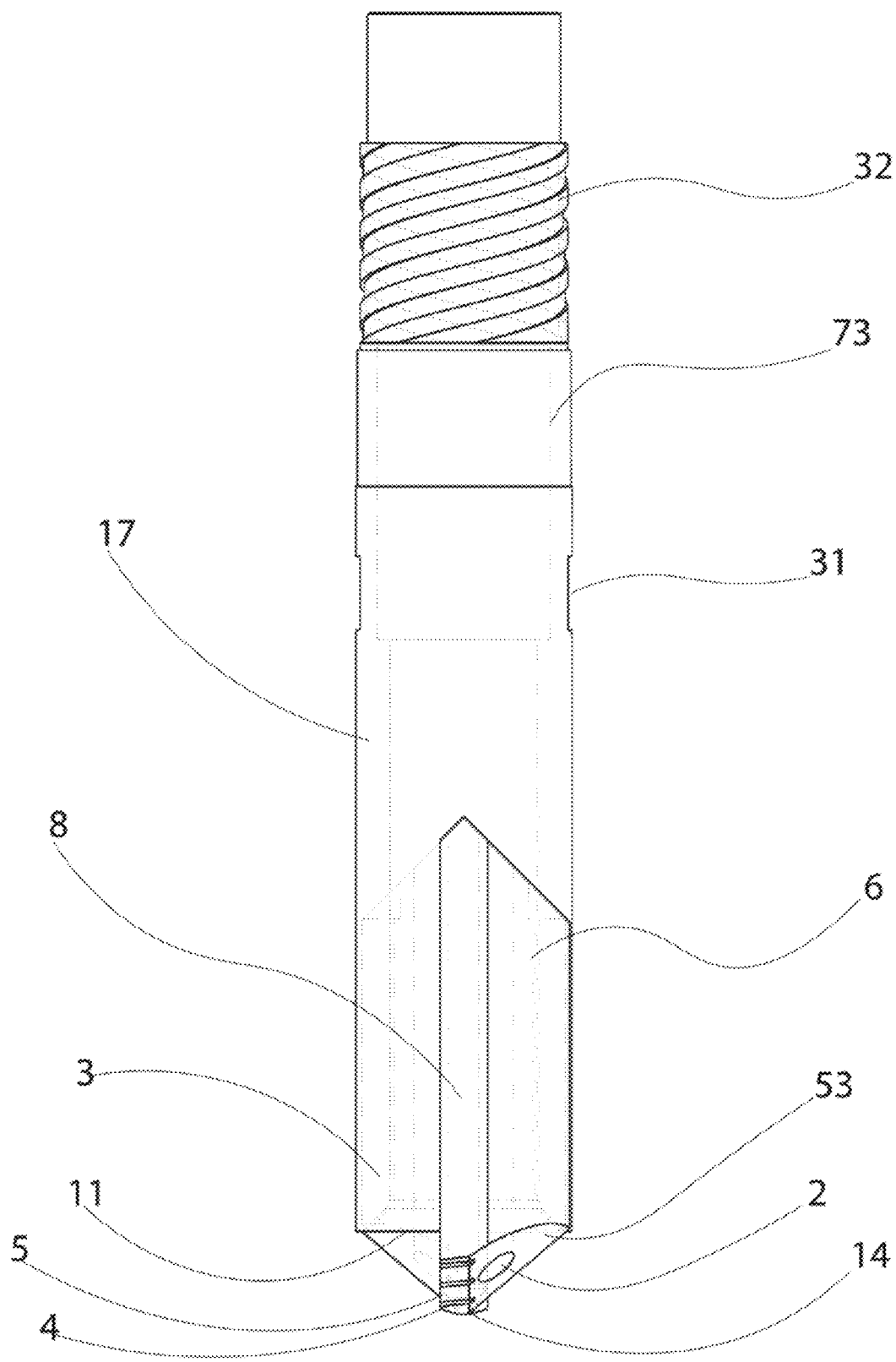
Figure 11a,

IN-SITU METHOD OF DRILLING TO COLLECT DRY SAMPLES FROM A NUCLEAR REACTOR CORE INTERIOR FOR ANALYSIS

TECHNICAL FIELD

The invention's field relates to the in situ sampling and characterization of activated metal alloys and graphite from a nuclear reactor core. In particular to a process method and system pertaining to nuclear reactor internal access utilizing a specialized long rigid angled sampling gantry in conjunction with hollow tungsten carbide drill bits with positively held cutting sampling heads for sampling and characterizing large nuclear-activated metal components. This unique sampling head and sampling train system allow for penetration through zircaloy, stainless steel, and carbon steels. It continues to cut and collect all drilling debris even when sampling from across multiple void spaces and layers of metal materials.

BACKGROUND

The nuclear power plant owners and operators are in the process of decontamination, decommissioning, and dismantlement of many of the nuclear reactor and process facilities throughout the United States, Canada, Europe, and Australia. These fission and fusion reactor nuclear facilities and their large, activated internal metal components have typically irradiated the core materials making them highly activated and chemically or radiologically contaminated. The development and implementation of an upfront characterization process step define the best alternative for the facility's final dismantling and decommissioning phase. The development of the detailed decommissioning plans includes the post-closure safety case that requires verification of the radiological inventory. The majority of the radiological inventory within the nuclear power plant facility is associated with activation of reactor core components, calandria, zircaloy pressure tubes, the concrete biological shield reactor vault, and the heat transport and the moderator system. The heat transport and moderator systems contain activation, fission product, and tritium surface contamination because of historical fuel pin ruptures and failures.

The upfront nuclear power plant sampling and characterization allow governments and international nuclear regulators to move forward with the nuclear-decommissioning strategy, clearly defining the risks and liability for activated metal alloy and graphite material removal from the nuclear reactor. The Nuclear Reactor Core Block's physical properties, such as mass and material type and composition and the radionuclide ratios, are produced using theoretical models for each material with decay periods of 10, 15, 20, 30, and 40 years from the shutdown. The activity values are calculated using neutron flux values and the radionuclide ratios for the material. These materials can be the metal samples from the internals of a nuclear fission or fusion reactors for waste segregation based upon activation product content activity of alloy materials from the nuclear reactor for the disposal of radioactive wastes at a reduced radwaste volume, being correctly sentenced and packaged to meet Waste Acceptance Criteria WAC and access the total activity summation and accurate activated waste level volumes of the reactor internal metal components such as zircaloy pressure tubes, stainless steel, and graphite.

Inaccurate data input into the simulated models can lead to an inadequate or incorrect nuclear activation activity distribution model. To overcome this problem, and for the model to produce significant results, accurate neutron flux values are required and precise material compositions and real metal samples. The activated material composition of the nuclear reactor core block's material composition is essential if the radionuclide ratios produced by the mathematical model is to be accurate. To facilitate this accuracy, information regarding the neutron activation analysis results acquired by the TruProBit® retrieves samples of mild steel, Boral, aluminum, stainless steel, and graphite obtained by the described nuclear reactor core sampling process by neutron activation analysis of the irradiated samples. The neutron activation analysis results of these irradiated real metal samples provide the actual current material composition of the nuclear reactor core block after many decades of operation, thus allowing to confirm the accuracy of the neutron activation mathematical theoretical model. The activation and contamination data obtained during the sampling process is reduced and transferred to reactor 3D models and drawings to show better and quantify the extent of the nuclear activation, tritium, or chemical contamination.

The sampling and characterization process arrangement samples, retrieves, and detects nuclear activation, elemental chemical analysis, or potential radioactive contamination at depth within the nuclear reactor core's activated metal components. This eliminates historical unknowns, increases worker safety awareness, and reduces radiological risks of reactor decommissioning and dismantlement, demolition and waste packaging, and shipment, precisely defining reactor decommissioning strategy focus and direction.

DESCRIPTION OF THE DRAWINGS

The invention is herein described, by way of example only, with reference to the accompanying list of figures and drawings, wherein:

FIGS. 7A, 7B, 7C & 7D are schematic illustrations of a plan and side views of one embodiment of the 11.11 mm hollow tungsten carbide vacuumed metal sampling head.

FIGS. 11A & 11B are schematic illustrations of side views of a replaceable quad helix 19 mm hollow tungsten carbide vacuumed metal sampling head in accordance with the present disclosure.

DETAILED DESCRIPTION

Figure 1:
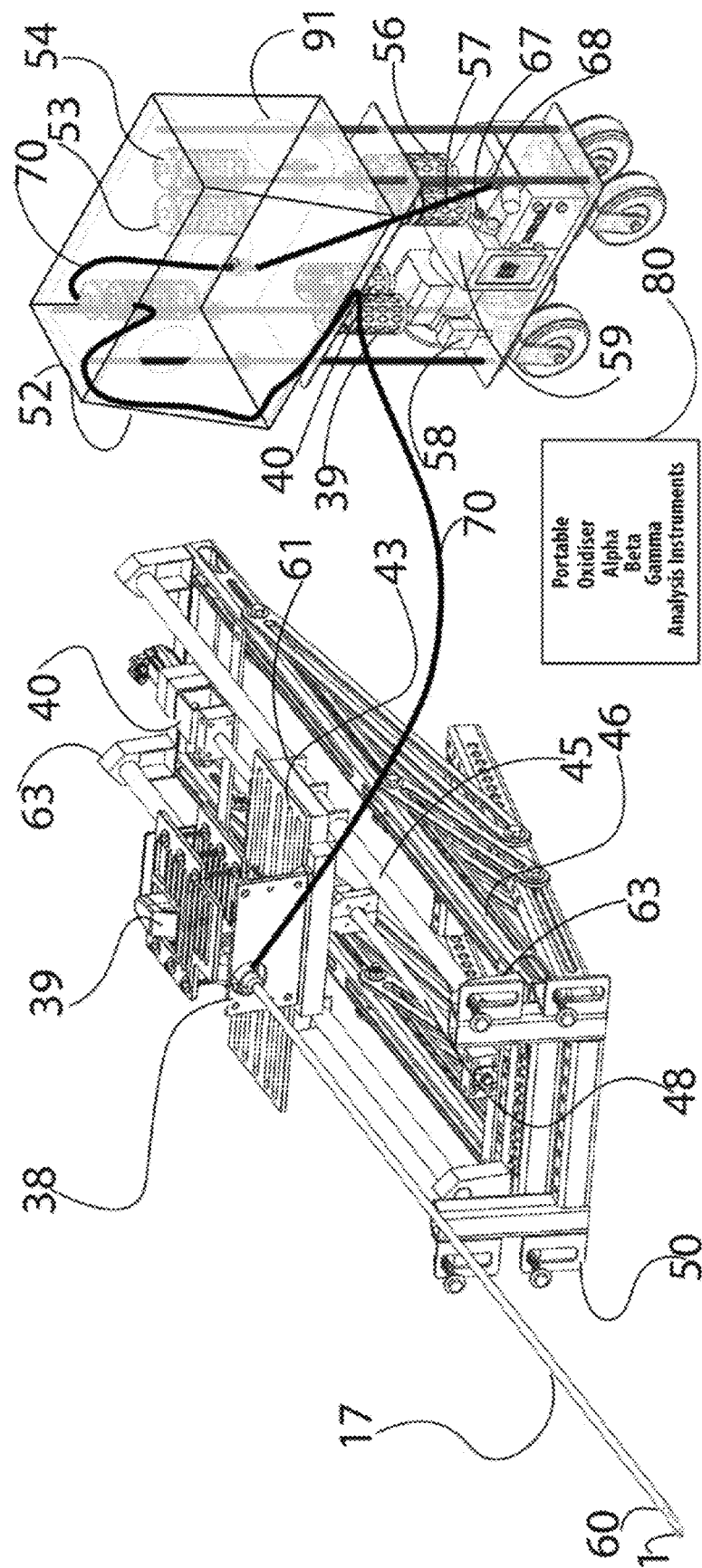
FIG. 1 is a schematic illustration of the reactor core sampling system and process in accordance with the present disclosure.

In general terms, the invention comprises and relates to the sampling and characterization of the nuclear reactor core activated metal alloy nuclear components and graphite moderator insitu and a process method and system relating to nuclear reactor internal access metal sample retrieval from across multiple alloy steel layers and void spaces. Outlined in the disclosure are the practical mechanical and mechanical configuration advantages, obtaining useful metal alloy activation results thereof, evident to those skilled in the art of nuclear power plant reactor sampling and characterization. In the present disclosure description, specific terms are used for conciseness, clarity, and understanding. Still, no unnecessary limitations are to be implied therefrom beyond the art requirements, and such words are employed for descriptive purposes herein. They are intended not to be limiting but to be broadly construed.

The nuclear reactor and activated component metal cutting and sampling drill bit, TruProBit® of the present invention can be used in the nuclear reactor sampling drilling system, in which the drill bit sampling head is guided by the cut hole wall or by the inner wall of an outer metal sleeving spanning void spaces, potentially filled with thermal insulation, asbestos, or fiberglass and to keep the hole open while traversing the void space. This sleeving allows the flow of vacuumed air to the metal sampling head, prevents blockage to deeper depths, and maintains a cool sampling head and metal component. The metal alloy nuclear reactor internals sampling and characterization technology process is a specialized activated nuclear material chemical, and radiochemical profiling drilling tool has four major components: a drill with a specialized metal cutting and sample retrieving head, hollow metal sampling drill bits, a sample collection unit contained inside a portable glovebox and a vacuum pump. The specialized hollow sampling head and sampling gantry support equipment in conjunction with mobile analytical equipment produces a metal sample of chemical or radiological activation or volumetric contamination activity through the nuclear reactor inner core metal components and interfaces. Dry cold air under vacuum is drawn down the profiling access hole and along the exterior of the drill bit body and the particulate air guides. The air is drawn down the deep hole to the hollow tungsten carbide sampling head, pulling the metal filings towards the particulate air inlets, then retrieved back along the interior of the hollow metal sampling head central air passage. This rapid vacuum airflow clears the drilled activated metal sample debris back along the drill's hollow shank center. The specialized hollow tungsten carbide nuclear reactor drill bit with a continuous airflow through an internal central drilling vacuum passage has one or more metal alloy filings, chips, and dust sample inlets arranged adjacent to the cutting edges to collect all of the activated metal samples as dust and metal filings of the metal material layer penetrated. The air slit grooves allow air to move toward the sampling head air and particulate guides and remove and retrieve chippings, filings, and metal dust. Airflow debris pickup maximizes the forward progress while promoting metal sample retrieval and negating the next incremental sample's cross-contamination. The clearance between the drill bit body and the sampled drilled deep hole reduces the friction between the drill bit body and the metal component. The carbide head diameter is slightly greater than the shank of the hollow metal alloy cutting and sampling drill bit, reducing the friction between the cut hole wall surface and the drill bit shank wall. The air inlet gap allows airflow toward the hollow sampling head to remove the cut metal chips and metal filings and cool the cutting drill bit and metal interface.

Figure 14:
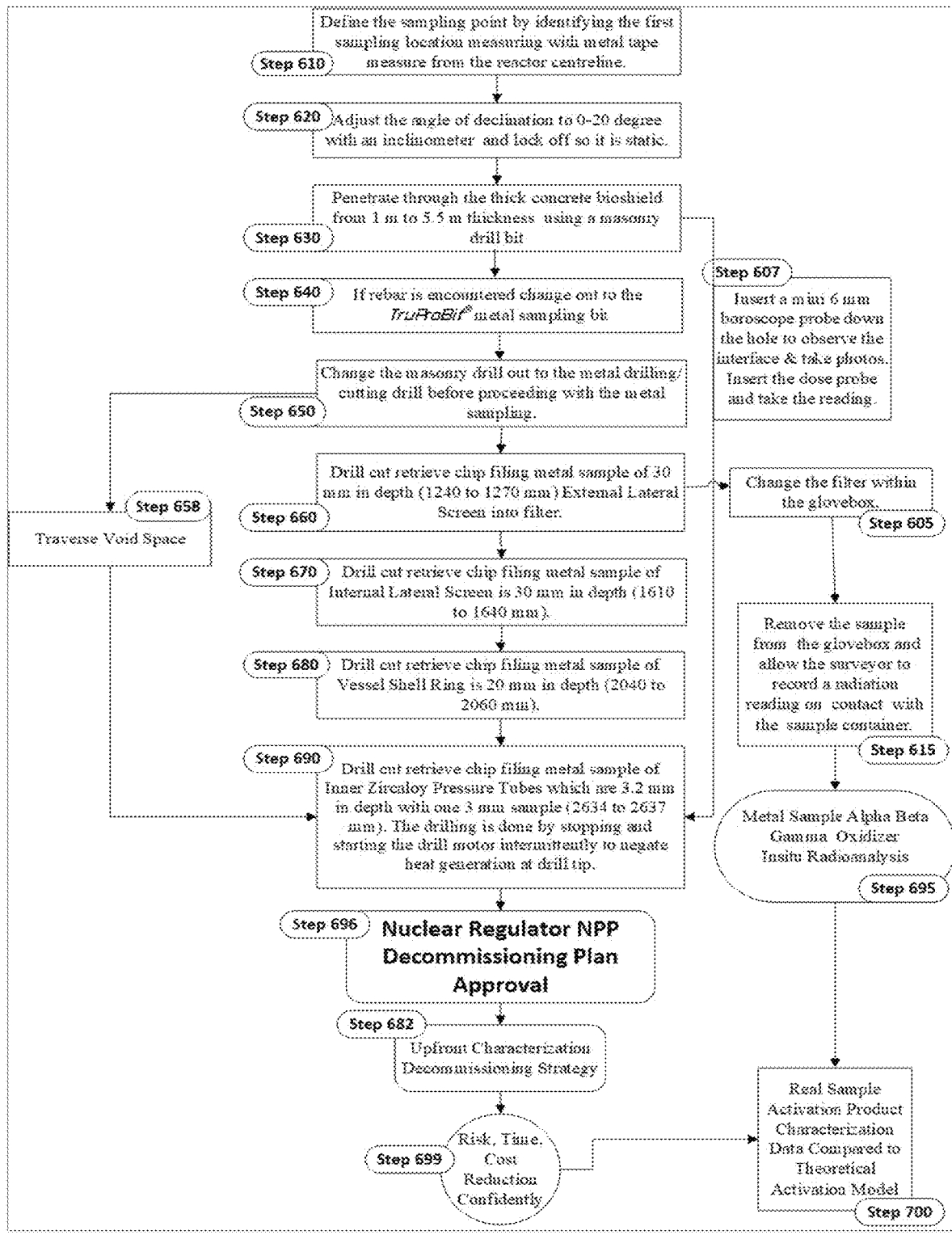
FIG. 14 is a process flow diagram for the metal sampling and characterization of a nuclear reactor activated metal alloy in accordance with the present disclosure.

In FIG. 14, the nuclear reactor activated metal alloy sampling and characterization process of the present disclosure is shown; the first critical step is for the present invention metal cutting sampling head and an angled sampling gantry to be anchored securely to the outer reactor wall to be penetrated and sampled. Start the sampling hole in the correct predetermined location $x_0$, $y_0$, $z_0$ to get to the right point in space required to obtain a zircaloy 2 sample from the point in space $x_1$, $y_1$, $z_1$. Step 610 defines the sampling entry point by identifying the first sampling location measure from the reactor centerline. In step 620, the adjustment of the sampling angle of declination is set to between 0 to 30 degrees using an inclinometer and locked off static. Step 630 involves penetrating the thick concrete bioshield from 1 m to 5.5 m thickness bioshield using a masonry drill bit. In Step 640, if rebar is encountered, the masonry drill bit is changed out to the TruProBit® metal sampling bit.

A 6 mm diameter mini boroscope HD probe is inserted down the hole to observe the interface and take photos, and the digital radiation dose recording is repeated as in step 607. Step 650 involves changing the masonry drill to the TruProBit® metal drilling/cutting/sampling drill before proceeding with the metal sampling. Step 658, the hollow metal cutting sampling bit spans the void space between the concrete bioshield wall and the nuclear reactor's metal outer. Step 660 involves the TruProBit® metal drilling/cutting/sampling head piercing through the outer metal layer of the nuclear reactor outer wall. The drill sampling head breaches the nuclear reactor containment with the cutting and retrieval of metal filing sample of 30 mm in depth, from 1240 to 1270 mm external lateral screen into a new filter. In some embodiments, the filters may be screwed into a housing and sealed tight with a latex O-ring to maintain containment of the metal dust and filings and the high vacuum's integrity. Step 605 involves changing the filter in the glove box. In step 615, remove the contained sample from the glovebox port 91 and allow the surveyor to record a radiation reading on contact with the sample container-repeat steps 607 and 658. In step 670, drill cut retrieves chip filing metal sample of internal lateral screen 30 mm in depth 1610 to 1640 mm. Steps 605, 607, 615, and 658 are repeated. Step 680 involves the TruProBit® cutting and sampling, and retrieving chip filing metal sample of vessel shell ring is 20 mm in depth 2040 to 2060 mm-repeat steps 605, 607, 615, and 658. In step 658, the drill bit traverses the next void space between nuclear reactor inner stainless steel vessel shell ring and then makes contact and sticks the point 14 onto the hard tube convex outer surface with step 690. At which point, the TruProBit® metal drilling/cutting/sampling drill rotates slowly at 60 rpm, cuts, retrieves chip filing metal sample of reactor inner zircaloy pressure tubes, which are 3.2 mm in depth with one 3 mm sample 2634 to 2637 mm. Repeat steps 605, 607, and 615. The metal chips, filings, and metal dust is collected for analyses by removing the first filter unit and dispensing the retrieved metal filing sample into a sample pot and counted.

Samples are dispensed and sealed within the counting containers, ready for analysis. The metal samples are analyzed in a low background area using insitu Alpha Beta Gamma radioanalyses. In step 695, the suite of calibrated radiometric instruments consisting of a portable gross alpha, gross beta, liquid scintillation counters for speciated beta analysis like Tritium or Carbon 14, and a gamma nuclide counting system 80 to analyze for activation products. Also, a mini video camera for taking photos, lights, gamma probe CZT 93 for dose rate, microdot dose probes 95 for dose rates, internal surface loose contamination 97 detection can be utilized down the reactor profiled sampling hole. By combusting the solid dry metal filings and metal chips sample and completely oxidizing the metal or graphite material using a portable oxidizer operated inside a fume hood, accuracy is increased by using the portable liquid scintillation counting system to analyze for Tritium and C-14 in near real-time as a sample from Heaven, with no subsampling or sample preparation or long sample storage. A representative metal sample from such a nuclear reactor core component using the sampling system may allow for the detection and quantification of metal activation products and tritium contamination at depth within the nuclear core metal alloy large, irradiated components in real-time. The metal sample, as chips, filings, and metal dust, is a sample from Heaven; no subsampling or sample preparation is necessary. Retrieval of the metal samples allows the production of actual activation product characterization data, compared to the theoretical activation model data 700.

The nuclear site upfront radioanalytical data is collated, and the activation product results are presented to the Nuclear Regulator as a site Nuclear Power Plant Decommissioning Plan for approval 696, which is streamlined via upfront characterization to affect Decommissioning Strategy 682 with the results of this data reducing the risk, time, and cost confidently 699. In one actual nuclear reactor characterization project, the above system and method in conjunction with a sample oxidizer and a liquid scintillation counter system to detect tritium at depth within the activated metal component in real-time. One embodiment takes samples of metal from a metal alloy object or reactor core component to be profiled at 1 mm increments at many points on the surface for the first ten metal discrete samples. A known mass of each incremental depth of metal chips and filings and metal dust sample is weighed on a calibrated balance. From the start of sampling to the completion of the analysis, a total time of 15 minutes per sample is observed, which is a vast improvement in time and cost as there is no other method for nuclear metal sampling and retrieval and insitu radioanalysis of hard activated metals and with total tritium capture.

The metal cutting sampling head comprises a machined tool steel holder having a bifurcated front end of machined tool steel to hold the hollow tungsten carbide cutting head. The tungsten carbide holder has machined slots to accept and mate snuggly with the hollow carbide sampling head. A long hollow drill bit shaft body is configured at the backend with a quick-fit connection fitting into the rotating electric drill motor for sampling the internals of a nuclear fission or fusion reactor with radwaste characterization and segregation the objective. It is relatively easy and apparent to a skilled operator in the art and from the description and perusing the drawings that an understanding may be attained of the technical difficulties surmounted by the provision of a means to penetrate and retrieve metal alloy or graphite samples from nuclear-activated metal materials. The metal sample obtained by the sampling system mechanism and process, using the hollow tungsten carbide head configuration, construction, and combinations and sub-combinations and parts comprising the present invention, is the preferred illustrative embodiment. These elements and objects utilized in the outlined demonstrative best mode are detailed descriptively and illustratively in the diagrams and figures described. A self-centering tungsten carbide sampling head 1 to drill into and hold the point of contact with the curved or angled activated metal surfaces encountered in profiling through the nuclear reactor bioshield and nuclear reactor core vessel and components. Concrete only masonry drills are rather dull when new since they are meant for hammer drills and concrete, not deep steel alloys. The challenges encountered penetrating through nuclear power plant highly activated radiologically contaminated hard metal alloy components using a TruProBit® to cut, collect, and capture all of the sampled and penetrated activated metal alloys or graphite with the critical use of the pair of sampling head curved particulate air guides configured to guide the air and particulate forward to just behind the metal sample head cutting edge. This narrow air gap clearance allows the capture of all metal particulate, metal dust, metal chips, or filings and fugitive tritium inside a replaceable cartridge body within the drill bit body. The hollow metal cutting drill bit retrieves representative metal samples from the highly activated extremely hard nuclear component alloy steel materials from nuclear fission and fusion reactor cores.

A specialized long rigid angled sampling gantry 50 in conjunction with hollow tungsten carbide drill bits used for deeper depths of metal sampling; the sidewall air inlets complemented with radially opposed 2 mm air slit grooves running axially along the tungsten carbide holder exterior. The air slit grooves serve to allow air to be drawn to the front end of the drill bit sampling head when buried deep within activated nuclear metal components of an inch or more in-depth. The grooves guide air for the metal chip, filing and dust removal away from the cutting edges and drawing filings and collecting all metallic dust while maintaining a cooling action to allow dry metal sampling with drilling and metal particulate retrieval with capture and progress through the metal component or layer sampled from across multiple void spaces. There is nothing off the shelf to anchor the drilling mechanism securely and drill and penetrate dry the many metal layers and void spaces encountered before penetrating the surface of the target highly activated zircaloy pressure tubes. The metal cutting sampling head 1 in conjunction with an angled long rigid modular sampling gantry 50 holds the hollow long sampling head drill bit in a locked-off static position on the nuclear reactor bioshield wall during the internal nuclear reactor sampling operations by use of the drill, hollow metal cutting drill bits with dry airflow for metal alloy filings retrieval and activation analysis and withdrawal of the sampling head from the large metal component. A shear action or mechanical or heat stress being necessary to dislodge the same accidentally avoided using the described sampling head configuration locked off to sample using the sampling gantry adjustable rail mechanism keeping drilling forces applied along one axis. The present invention provides a simple construction sampling cutting head for nuclear core metal alloy penetration producing filings and chippings, dust and powder of the metal alloy layers, with retrieval as a metal sample as layers are traversed sequentially at deeper depths. The present invention and metal sampling process use the specialized metal cutting aspirated hollow tungsten carbide sampling head of the present invention for accurately drilling deep holes of small diameter to depth, e.g., holes of 11 mm up to 38 mm diameter and up to 1651 inches deep, through activated metal alloys and generally for sampling through stainless steel, tungsten, nickel-copper alloys, annealed steels, carbon steel and softer metals like aluminum, Boral sheet, and lead.

The tungsten carbide specialized hollow sampling head 1 is used under rotatory action to cut metal filings and chippings and penetrate the hard metal component surfaces and volumes. No cross-contamination between reactor core layers occurs as the metal sample is drawn immediately from the front of the sampling head without losing the metal sample from behind the cutting drill bit tip to the inline sample collection filter. The nuclear core metal samples are continuously retrieved using a specially designed glove boxed vacuumed sample retrieval unit. Sample filter change-out inside the containment box prevents cross-contamination of the retrieved samples using clean connecting tubing and a new filter for each separate metal sample retrieved. A dry air/nitrogen gas stream is used to retrieve the metal filings and chippings. Anti-pyrophoric conditions setup at the sampling head and no circulation medium is required with this sampling process; therefore, the only by-product from drilling is the metal sample with no spread of or the liberation of contamination or highly activated material or tritium due to the unique sampling head design and metal sampling process.

In one embodiment, a method and system is disclosed to volumetrically sample and characterize the large metal components from the nuclear reactor core of a heavy-water nuclear reactor and obtain the total radioactive speciated activation product content of the reactor core irradiated metal materials. The method comprises drilling into the nuclear reactor's side or laterally by penetrating and retrieving metal filings and chippings of sampled activated metal material, sampling activated metal from the drill point at predetermined incremental intervals, and analyzing the activated metal sample. Such an embodiment may be accomplished by using a precisely controlled rate of feed rotary drill with a specialized cutting and sampling head, drill bits of lengths up to 7 meters, an angled sampling gantry for angled drill bit penetration, and to target distant metal component targets behind walls and void spaces within the nuclear reactor pressure vessel, with the dry vacuum pump to maintain rapid airflow and vacuum at the TruProBit® metal sampling head.

The embodiment in conjunction with portable chemical and radiometric instruments produces discrete individual metal alloy samples or a profile of activation product and tritium radiochemical or chemical elemental contamination through the metal layers in millimeter discrete samples collected as 1 mm consecutive sequential incremental samples from the front and back metal surfaces. Also, as a practical example, to be able to stick a point and not waltz or skid over surfaces, but to penetrate the convex tube outer surfaces and to allow penetration and retrieval of metal filings and chippings and metal alloy dust of sample of the zircaloy pressure tubes or reactor component targeted for sampling and characterization of the nuclear facility radio-chemical and radiological inventory. The invention comprising sampling head and sampling gantry in conjunction with a portable glove box to house the sample filter manifold can remove discrete metal samples from the Heavy Water Reactors or Pressurized Water Reactors. The diameter of the drill bit to depth ratio of 650 to 1 is attained with a TruProBit® of d:D 10 mm:6500 mm. The collection of all metal particulate from nuclear reactor sampling operations into specialized filter units housed in a mobile glovebox mitigates contamination release on depositing the sample from the filter into the sample pot separate from the uncontaminated clean normal nuclear facility operations working area. The TruProBit® produces dry representative samples in the form of metal filings and chippings or metal dust and powders form from metal material layers up to 100 mm thick or greater of stainless steel from across void spaces of a few millimeters or up to 2000 mm distant and continue penetrating and retrieving samples across additional void spaces and physical metal reactor containment layers. Sampling the reactor internal activated metal components includes the mild steel casing, high-density concrete, metal rebar, reactor tank inner and outer walls, the calandria reactor core and the horizontal zircaloy pressure tubes and going entirely through the reactor internal void spaces with the extraction of all metal filings and chippings samples. The collection of all samples in this dry manner reduces the radiological risk, prevents and eliminates the spread of contamination. Sampling establishes the radioactivity profile of each activated material representatively, surgically, and cleanly. The nuclear reactor hollow metal sampling drill bit 60 consists of a drill tube body 17 and a tip 1. The hollow tungsten carbide cobalt tip 1 is mounted on the proximal end of the drill tube body 17. The invention is generally directed to an insitu process and system for the dry sampling & characterization of nuclear reactor core irradiated zircaloy pressure tubes, hard activated alloy metals, and graphite from nuclear reactor core internals. The hollow tungsten carbide drill bits may comprise a steel tube tool holder, a hollow tungsten carbide section with a hard material cutting head, for example, a tungsten carbide head, attached at the backend of the hollow shaft of the drill bit is a shank to reliably and quickly connect to a tool holder or a drill or the like, for example, a rotary only drill, a rotary percussion drill or a rotary hammer drill. The hollow shank allows the drill bit's attachment to the drill and provides airflow and particulate movement to the glove boxed inline filter sample capture units. The drilling of 7 meter deep narrow holes of 11.11 mm diameter and retrieval of the cut filings and chippings of metal material from the bottom of the hole by providing a single solid tungsten carbide cutting body set 3 mm forward of the tool holder. The hardened heat-treated tool holder is axially set back 3 mm from the tungsten carbide, cutting leading edges, and radially set back from the outer diameter particulate air guide supports. The auxiliary edges defined by the tool holder metal particulate curved air guides extending along the obtuse longitudinal angle of the hollow tungsten carbide sampling head to form particulate capture right up to the cutting edge so all metal filings and chips, particulate are collected by the rapid inflow of dry air into and along the drill bit and into the sample filter manifold within the containment glove box.

The configuration of the cutting head angles and sampling head zones of particulate capture clearance of air intake from down the drilled holes cut surface and the outer body of the hollow shank of the drill bit according to the invention requires less power to turn and drive and cut due to the efficient clearance of drill cutting debris instantly cleared from the front end of the sampling head before the next rotational cut. It should be understood that while the invention has been described in conjunction with specific embodiments, it is apparent that many alternatives may be derived. Accordingly, the invention is intended to embrace all such alternatives, modifications, and variations that fall within the claims' scope. Modifications and variations will be apparent to those skilled in the art and method of activation product and contamination profiling characterization of the reactor core and irradiated component materials containing or possibly containing activation products or radiochemical or chemical contamination spread by fuel pin rupture coating the cooling systems contact surfaces and tubing in activation and fission product radionuclides of varying half-life duration. A nuclear reactor hollow activated metal sampling drill bit 1 of the art is shown in FIGS. 1 through 11. The TruProBit® cutting sampling head is a solid piece of tungsten carbide 1 forming the drill bit's cutting body, having an hourglass figure of 8 shape with the main opposing sampling cutting edges 7 defining the main cutting edge. Rake surfaces and relief surfaces define the major cutting edge. Major facets define each rake surface and relief surface. The main cutting edge includes a set of chip breakers 4 on each edge and radially offset from each other to facilitate the metal filings and chipping and metal dust of the hard metal alloys, stainless steel, zircaloy pressure tube activated samples. A primary planar rake facet 3 is on the end of each of the two cutting edges, and a pair of 3 mm holes 2 through the body of the tungsten carbide allow drill debris retrieval. The body is kept cool by the rapid flow of air through the tungsten carbide body that comprises these rake face facets 3, adjacent to each of the two cutting edges 7, and defines the main portion of the metal sampling head body cutting edge. The remaining portion of the leading cutting edge is defined as the self-centering pilot point 14 at the apex of the two radially angled straight swept cutting edges. A further aspect of the disclosure provides a drill bit, including a robust air-cooled sampling cutting head according to the disclosure's first aspect. The auxiliary edge is defined by the sample head slot metal particulate curved air guides extending along the obtuse longitudinal angle of the hollow tungsten carbide sampling head. These particulate air guides enhance particulate capture by running right up to the cutting edge, so all particulate is collected by the rapid inflow of dry air into and along the drill bit and into the glove box sample filter manifold. The advantages of the disclosed invention may include one or more of the following. An advantage of the two identically shaped cutting arms 5 of the present invention's sampling head is that the metal cutting forces during sampling head 1 rotation on the cut are evenly distributed across both cutting edges 7 and throughout the bulky one-piece tungsten carbide body 1. The heat shock and vibrational forces of drilling resistance using dry air only with no lubrication to remove the cut metal filings and chippings of the sample. This even distribution of the frictional heat cutting force over one larger cutting edge with air holes 2 and particulate air guides 15 allowing the free flow of air and particulate from the cutting edges backward through the hollow body of the drill bit with cutting edges than those of conventional metal heads leads to reduced breakage of the cutting edges. Additionally, the configuration of the cutting head angles and sampling head zones of particulate capture clearance of air intake 11 from down the drilled holes cut surface and the outer body of the hollow drill tube body 17 of the drill bit according to the invention require less power to turn and drive and cut due to the efficient clearance of drill cutting debris being instantly cleared away from the front end of the metal sampling head before the next rotational cut. According to one aspect of the invention, the dry air hollow drill bit activated metal sampling head improves the robustness, penetration, speed, and overall lifecycle of the drill bit. The sampling equipment and drill bits are hollow and designed to allow a rapid vacuum air stream. High vacuum airflow at the sampling head tip negates the spread of contamination, minimizing the production of sampling secondary wastes and sample cross-contamination issues. The use of a TruProBit® achieves this' a specialized metal alloy cutting hollow tungsten carbide drill bit, in conjunction with a mini gantry angled robust base for drill bits spanning 2-meter lengths in one continuous drill penetration and retrieve and capture metal chipped filings and chippings metal sample inside a hermetically sealed containment glovebox 52 to negate the spread of radioactive metal dust or asbestos. The tungsten carbide hollow sampling head is a metal matrix composite, the tungsten carbide particles are the aggregate, and metallic cobalt serves as the matrix and does not wear quickly sampling through carbon steels and wears less than standard steel tools. The other end of the drill tube body 17 is provided with a shank 27 having a machine-specific quick coupling disconnect design. The shank 27 mounts to a tool holder on a coupling rotary spindle of the drill motor 39, coupled to a drill bit 60 in a known manner and supplied with vacuumed air via vacuum pump 59.

Turning to FIG. 1, the first aspect of the invention illustrated is a sampling gantry system 50 for employing some of the present invention's embodiments. The drill motor 39 is a rotary drill with a variable speed gearbox to allow the metal cutting sampling head to penetrate hard metal surfaces at the correct feed and rotational rate. The mini gantry drill press support as shown in FIG. 1 Reactor Core Internal Component Sampling System and Process under the present disclosure, keeps drilling rotational forces centered between heavy rigid fixed arms 46 along which the drill bit 60 is moving along one axis directly in and out of the sampling profile hole. The drill press mechanism guarantees a perpendicular profile to the surface, no downhole snagging by loss of positional tolerance over multiple control motors of position, and missing the hole center, reducing to one motor axis of motion allows more precise sampling hole rate of the depth of cut control. The mini gantry drive mechanism 40 offers an independently controlled mechanism for presenting the drill and core bit to the material. The robust drill rig gantry smoothly and effortlessly presents the sampling mechanism into proximity to the material's surface to be penetrated and sampled. The gantry mechanism is composed of 2 supports or solid metal rails 45 along which the drill bit fixed carriage base 43 and the chassis of the drill motor 39 rides smoothly. The fixed carriage base 43 can be locked off securely using O-ring clamps 62 to provide a fixed base from which to proceed with sampling before being advanced successive depths using the drive mechanism 40 and ball screw thread 48. The fixed carriage base 43 is supported on linear bearings at 4 points 62. It provides reliable solid support and carriage guidance to and fro into and out of the core of the nuclear reactor activated metal waste and tritium contaminated metal component, dissipating vibration and torque. The supporting mini gantry rail arms 45 mounted in solid steel rail supports 63 that provide mechanism stiffness and rigidity and drill bit jack mechanism fixed points to pull off rather than robot arm motors.

The sampling gantry 50 presents the sampling head 1 of the drill bit 60 as a press mechanism and provides more control over drilling forces and penetrating angles, creating stability to holding a tight tolerance of less than 0.1 mm. Drill forces are focused on one axis of movement, so systems control of sampling can be monitored dynamically to provide a tactile real-time response to metal filings and chippings sample retrieval. The metal drill bit's penetration depends upon retrieving the cut metal filings and chippings from 1 mm to 7.0 m sampling depth and traversing multiple void spaces multi-directionally, as shown in embodiment 1 in FIG. 2 and FIG. 3, respectively.

The second aspect of the presently disclosed invention is provided, wherein the sampling head defines the cutting arms 5 and cutting edges 7. The cutting arm has a peripheral rake edge generally parallel to the central axis of the drill. The two max-V grooves and facet design illustrated in FIGS. 3 and 4, 19 mm Hollow Tungsten carbide vacuumed metal sampling head orthogonal view in accordance with the present disclosure, the tip end contacts with the bottom of the hole being formed, and defines a bottom clearance space into which air flows between the drill tube body 17 outer wall and the cut wall of the hole. The airflow around the cutting arms 5 and edges 7 flows along and over the relief edges and faces picking up the metal cuttings, metal filings, metal chips, and metal dust into the airflow and back along the center of the hollow drill bit from the airflow entering the bottom space via the air gap between the drill bit tube body 17 outer wall and the cut wall of the hole. The inlet air passage is defined between the lowermost edge of the secondary flank surface and the hole bottom and may provide a cutting sampling head for a hollow drill bit 60. The TruProBit® sampling head 1, when locked off static in the drill coupling 65 of the drill motor 39 on the fixed carriage base 43, can be locked off securely using the O-ring clamps 62 to provide a fixed carriage base 43 from which to proceed with sampling. The bit 60 is advanced successive depths using the drive mechanism 40 and ball screw thread 48 with an independent separate control system for delivery of the sampling head 1 of the drill bit 60 to the surface of the nuclear reactor activated tritium contaminated metal waste component or metal layer surface. To minimize the amount of power required to turn and drive the drill, the hard-hollow tungsten carbide cutting sampling head comprising two identically shaped cutting arms extending radially from a common central axial point 14, each cutting arm comprising a cutting edge 7 extending outwardly and axially backward from the common central self-centering point axis A-A'. Each sampling head cutting arm 5 is extended in a straight unbroken line from the self-centering central axial point 14 to the side chamfers 8 of the sampling cutting head. Each sampling head cutting arm 5 may comprise one rake facet 3 falling axially away from each of the two cutting edges 7, wherein each rake facet 3 comprises a side face section with a 3 mm air hole 2 behind each cutting arm 5. The two trailing rake faces of each sampling head cutting edge 7 may be angled backward about the longitudinal plane of the sampling head cutting arm 5 angle of between 5 degrees and 45 degrees. The cutting arms 5 are of equal angular spacing apart from each other radially about the sampling head's central axis. Each sampling head cutting edge may comprise one side cutting face that forms a zone of drill debris air influx and introduction into the chamfered curved tube face inlet 13 to immediately remove filings and chippings or filings through the lateral particulate air guides 15. These air guides add considerable strength and durability to sampling head 1 while cutting deep holes through stainless steel. The sampling head 1 cutting arms 5 also comprises side chamfers 8 on and between the radially outer face and extending to the rotationally trailing side face to prevent drill bit blockage, clogging, and binding of the drill bit 60.

Figure 2:
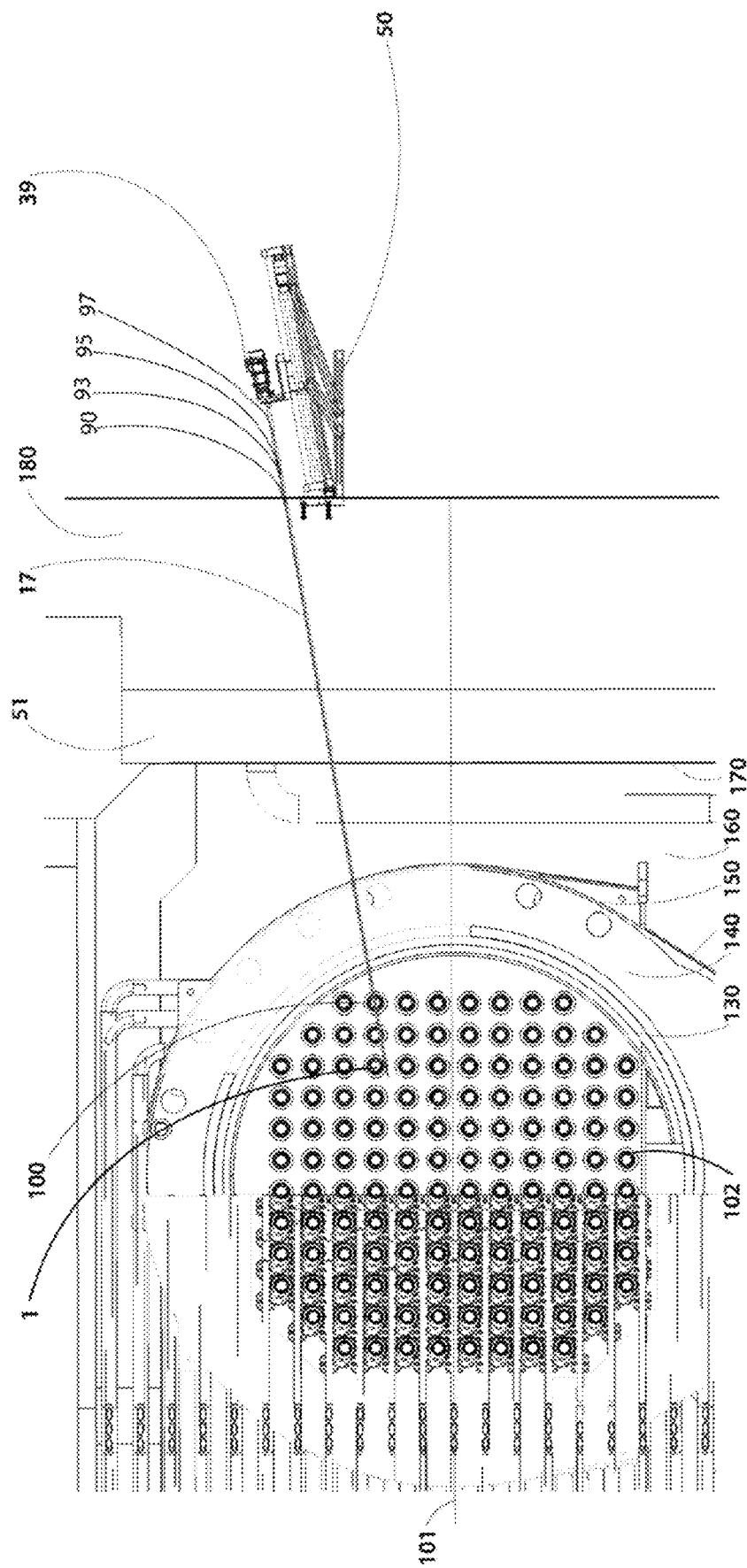
FIG. 2 is a cross-section of the drill bit penetrating a zircaloy 2 pressure tube outer for retrieving a sample. It shows an example of a profile through the outer bioshield to the nuclear reactor core internals with the drill bit at 15° to sample the pressure tube.

Turning now to FIG. 2, the cross-section of drill bit penetrating Zircaloy 2 pressure tube outer for retrieving a sample shows an example of a profile through the outer bioshield to the nuclear reactor internals. The drill bit is set at 15° declination to Sample the pressure tube; herein is a process illustrating the method of using the system of FIG. 1 to penetrate sample and retrieve filings and chippings of metal alloy samples from inaccessible high radiation nuclear core components. An operator uses a sampling gantry 50 and the drill bit 60 with 1 to drill into the irradiated reactor core internal metal alloy or graphite activated components. The hollow tungsten carbide sampling head 1 with 60 to a predetermined metal cut and sample depth. For instance, samples of zircaloy pressure tube 102 from the nuclear reactor core 100 internals can be sampled discretely or profiled at predetermined depth increments, e.g., 1 mm, 3 mm, 10 mm, 20 mm, 30 mm from across void spaces between reactor core irradiated metal layers and components. As the drilling and sampling end of the drill bit head 1 drills down to the required depth, rotational drilling action of a large metal cutting drill causes the activated steel alloy or graphite material below the sampling cutting head 1 to manifest as metal filings and metal chips or metal alloy dust and powders of the nuclear reactor metal alloy component. The vacuum air adapter 66 is connected to the drill motor 39. The hollow metal sampling drill bit 60 fits snugly in at one end of the vacuum air adapter 66, which is in concentric axial alignment and can be replaced and removed by being coupled and decoupled to the drill motor 39 via SDS+ shank 28 or by screw threads or another suitable coupling method into the drill coupling 65 allowing changeout of the sampling head drill bit 60. During metal sample retrieval operations, the drill motor 39 rotates and drives the drill bit 60, and the vacuum air adapter 66 remains static while the coupled SDS+ shank 28 rotates within the connected hermetically sealed air adapter, transferring metal filings and metal dust to the sample filter via the rapid airflow, created by the vacuum pump 59 that causes a vacuum suction in the vacuum connection line 70, which is in hermetic communication with the airflow passage 20 of the drill bit head 1. The vacuum within the airflow passage 20 causes the activated metal alloy or activated graphite filings and chippings and filings flow up the airflow passage 20 and exits the opening 23 of the drill bit 60 through the disposable plastic vacuum line 70. The sampling of the internal reactor materials' metal layers at greater depths may be advanced via the drive mechanism 40, turning the ball screw thread 48 causing the drill carriage 61 to incrementally proceed down the rigid steel rails 45, supported on solid steel support rails 63. This present invention is not limited to the standard sampling and characterization system process configuration described herein but can be readily applied to an assortment of systems and applications by those skilled implementing the art.

On the increasing depth of penetration of the sampling head 1 into the metal material layer of the nuclear reactor to be penetrated and sampled, the drill motor 39 is mounted on the adjustable drill carriage 61 and is locked off static via O-ring clamps 62 to allow sampling to proceed from a solid, immovable base. The drill tube body 17 is hollow, and the air is pulled by the vacuum through the hollow carbide sampling head, through the drill tube body 17, and through the rotating hollow backend of drill bit shank 28 with an air adapter. This air adapter allows the drill bit 60 to rotate while maintaining an airtight vacuum via a dry vacuum pump 59 pulling a vacuum of at least 27" Hg and 96 CFM cubic feet per minute at inlet 68. The air flows through the rotating connection of minimal contact surfaces with vacuum air adapter 66, connected via hollow plastic reinforced vacuum tubing 70 and through the hollow interior of the drill bit tube 17, drilling motor 39, and the drive mechanism 40 drawing metal chips and filings, and metal powders and dust as a representative metal sample from the frontend of the hollow sampling head 1.

The sampling system containment unit comprises a hermetically sealed glove box 52 containing the primary sample filter 53 and secondary filter 54 attached by connecting tubing to the vacuum pump 59. The manifold sample filter system has two purposes, the collection of discrete individual filings and chippings of metal samples from a known location and to contain cumulative drilling debris. The sampling drill bits 60, and filters can be rapidly switched accordingly, dependent on the mode of sampling. The portable glove box 52 contains the filters 53, 54 to collect the metal filings and chippings and filings and graphite filings and chippings and dust. The vacuum force developed by the vacuum source 59 draws the dust through the port and the vacuum line 70, where it can be collected on the filter unit 53. Thus, the filings and chippings of metal alloy or graphite dust can be quickly extracted away from the drilling end 1 of the drill bit 60 without fear of cross-contamination from the layers of metal or graphite above the sample area as would be the case with conventional drilling or boring equipment. A series of inline 0.50-micron 53 and 0.01-micron 54 filters or air scrubbers are placed within a portable containment glovebox 52 at the outlet exhaust to ensure complete particulate and tritium capture from the sampling head 1 to allow ease of transfer and contamination control with total metal particulate tritium and fugitive tritium capture. If the filter unit 53 comprises a plurality of filters mounted in series, the sampled metal filings and chips travel in the airstream to the first inline filter where it is collected and prevented from traveling to a secondary filter unit, which acts as a secondary barrier for the vacuum source 59. The air passing through the primary 53 and secondary 54 inline filters may pass through a tritium extraction unit 56 and volatile extraction unit 57 to trap all volatiles released during sampling. Furthermore, the exhaust 67 of the vacuum source 59 pump may have two 0.01 μm filters built into the pump mechanism to prevent any extraneous radioactive dusts from being released to the clean working environment. The sampling head 1 is set for optimum drilling angle, so the mini gantry drill press keeps drilling forces and drilling movement along only one axis, as shown in FIG. 1. Starting at the correct known position and keeping straight using rigid unbendable and extendable hollow drill tube body 17 comprising male and female tapered thread extensions so guarantees the desired sampling endpoint is reached by no flexion along the length of the drilled holes. Cross-contamination of the retrieved sample is mitigated by the air flowing over and along the outer wall with the drill bit cutting fragments entering the front cutting face. The cutting head's slow feed guarantees complete debris clearance on proceeding deeper dry of metal freshly removed along drill bit hollow center and maintaining the activated nuclear reactor component's structural integrity and the sampling machine itself. The geometry of the metal cutting hollow tungsten carbide sampling head used in the present invention may vary significantly based on hole diameter, material hardness, and material chip forming characteristics. Similarly, various facet designs can be used to practice the invention.

Figure 3:
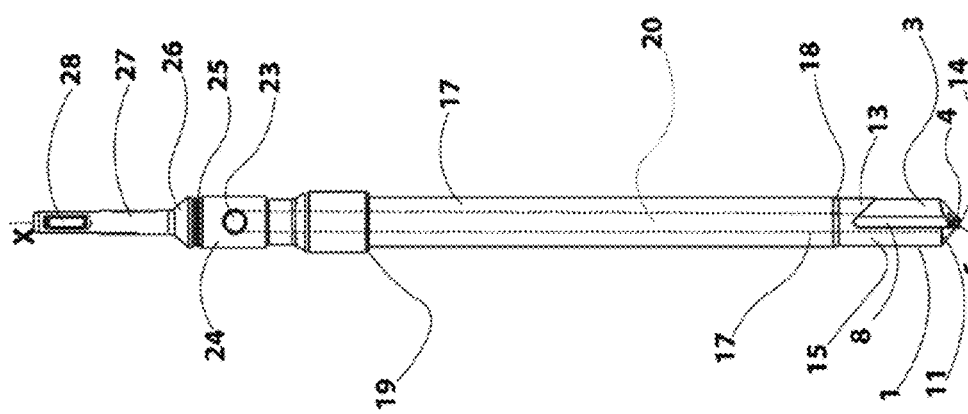
FIG. 3 is a schematic illustration of an orthogonal view of a 19 mm hollow tungsten carbide vacuumed metal sampling head in accordance with the present disclosure.
Figure 4:
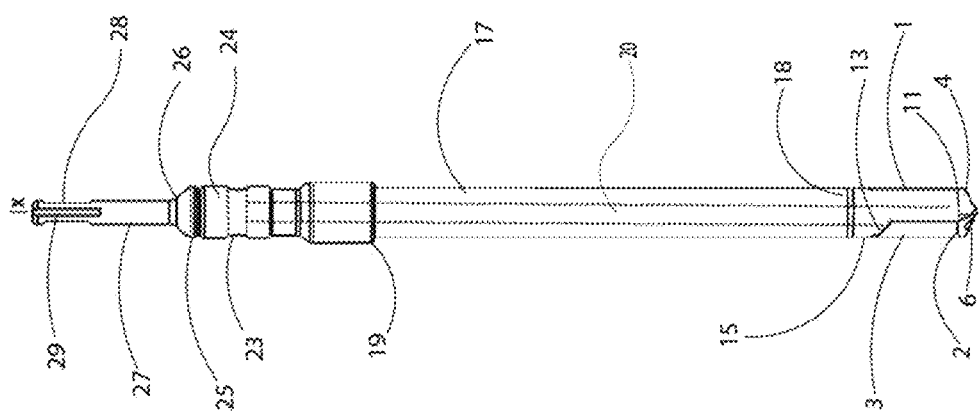
FIG. 4 is a schematic illustration of an orthogonal view of a 19 mm hollow tungsten carbide vacuumed metal sampling head in accordance with the present disclosure.
Figure 5:
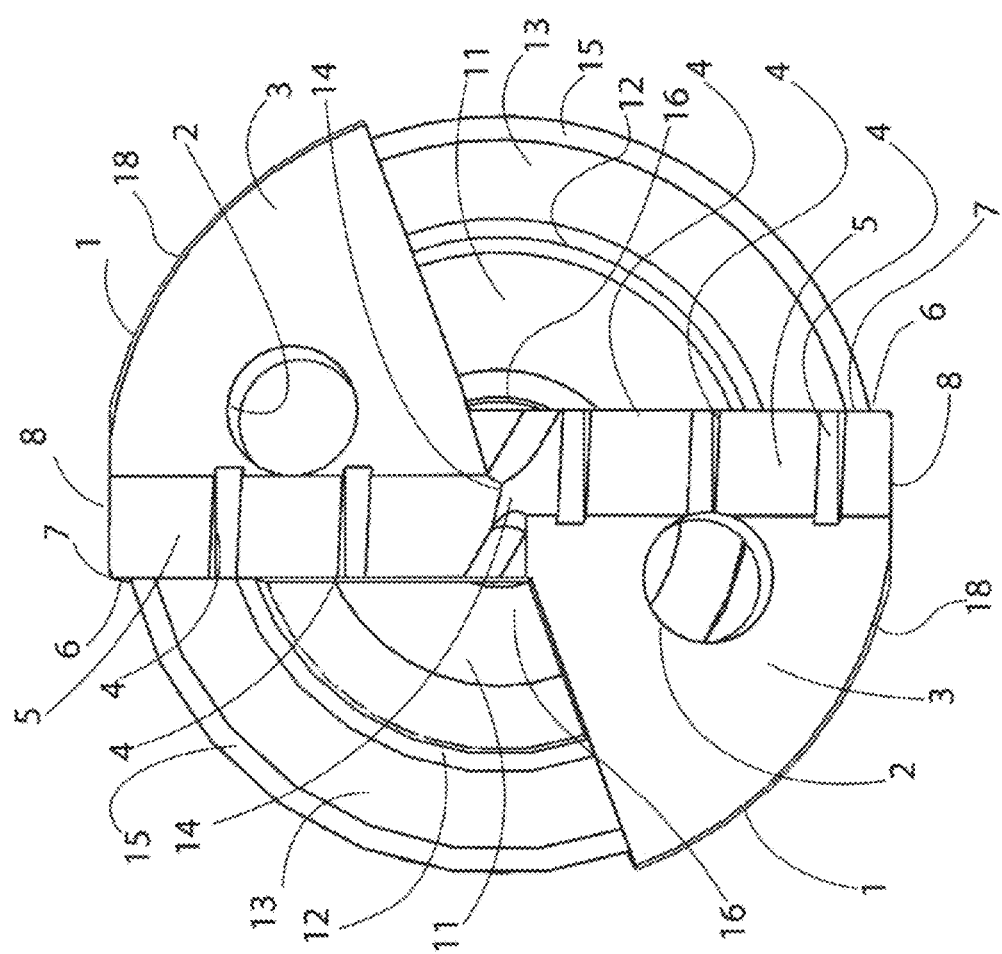
FIG. 5 is a schematic illustration of a plan view of a 19 mm hollow tungsten carbide vacuumed metal sampling head in accordance with the present disclosure.
Figure 6:
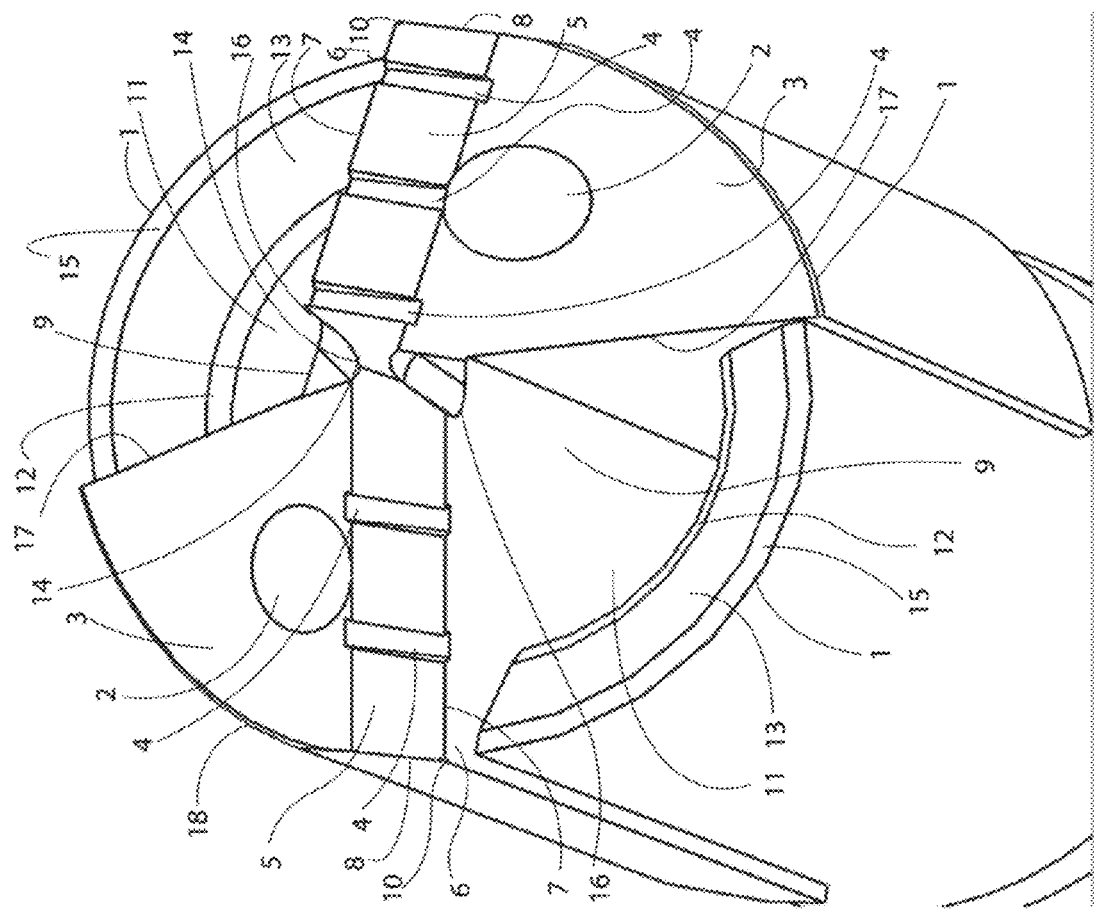
FIG. 6 is a schematic illustration of an orthogonal view of a 19 mm hollow tungsten carbide vacuumed metal sampling head in accordance with the present disclosure.
Figure 7A:
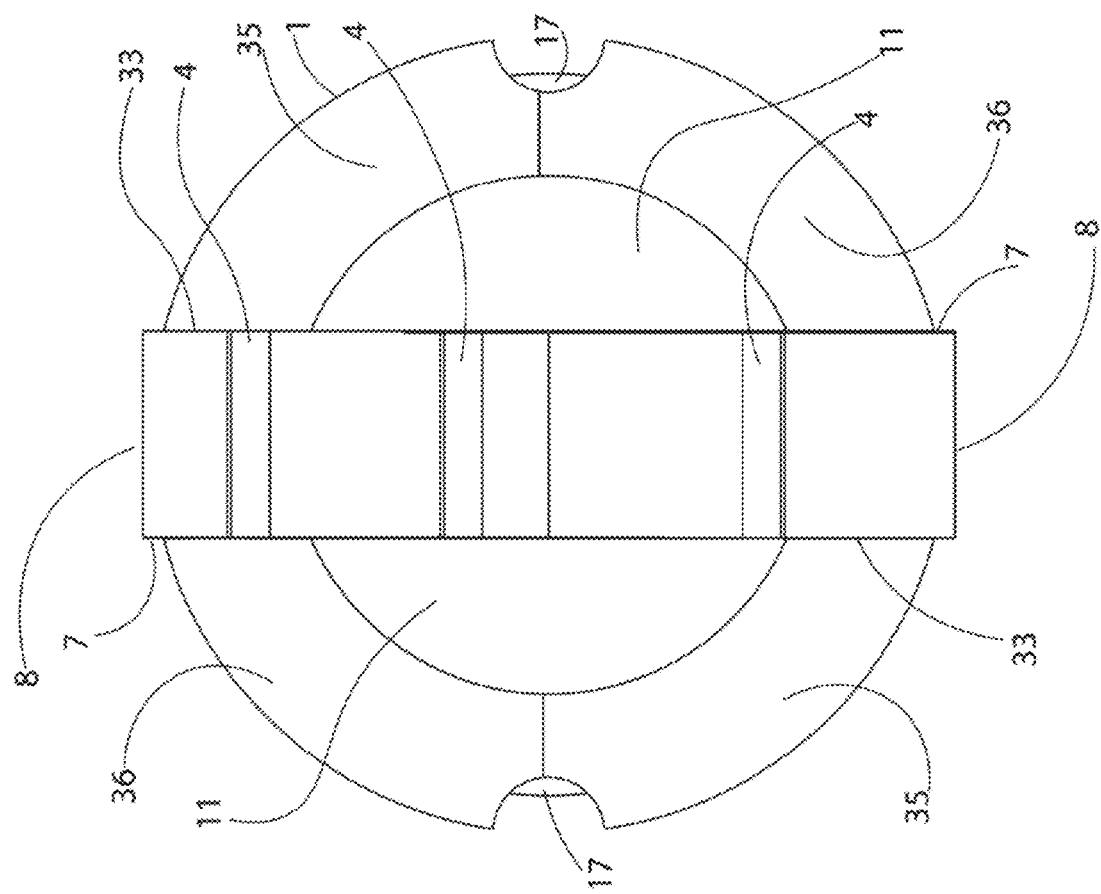
Figure 7B:
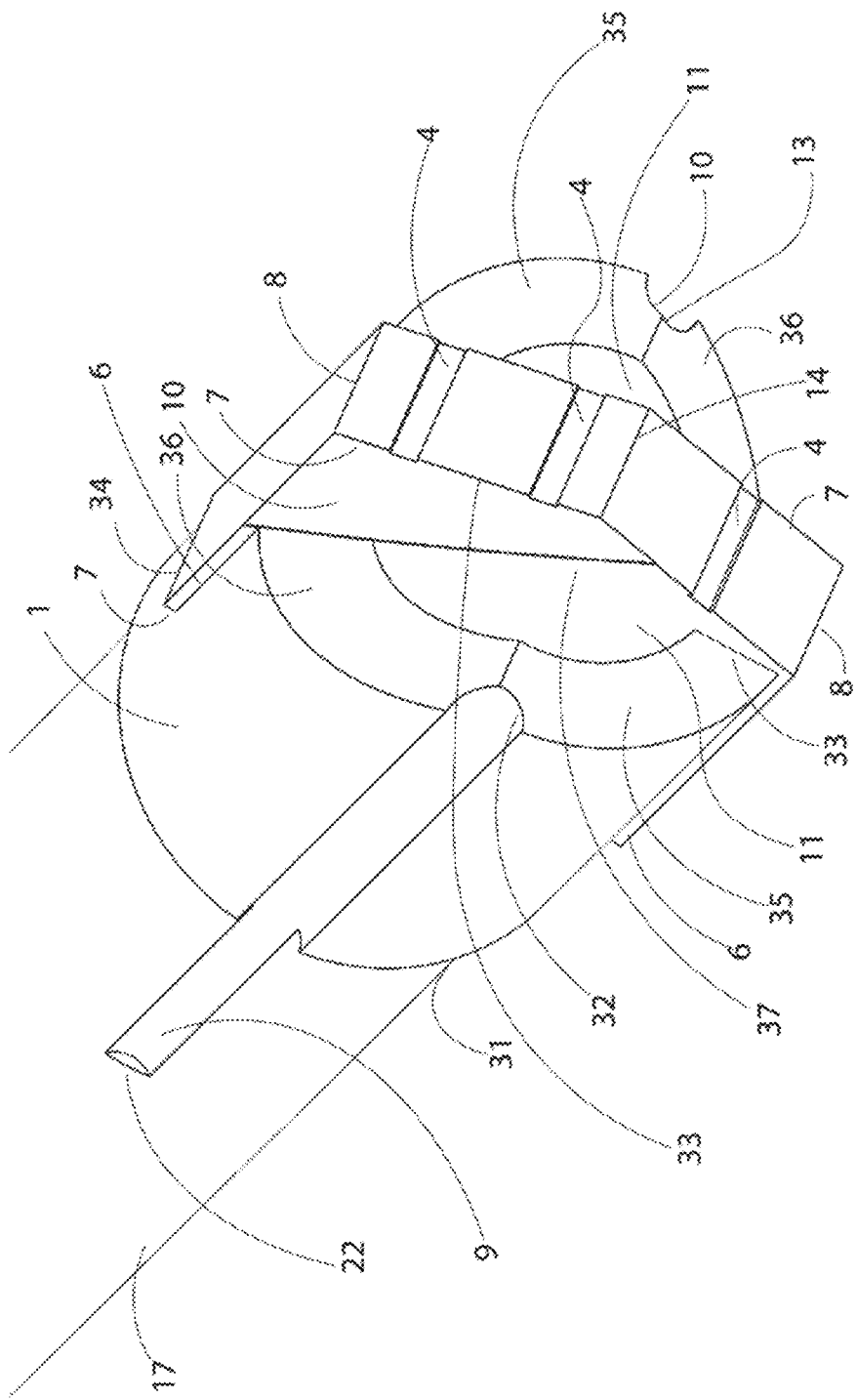
Figure 7C:
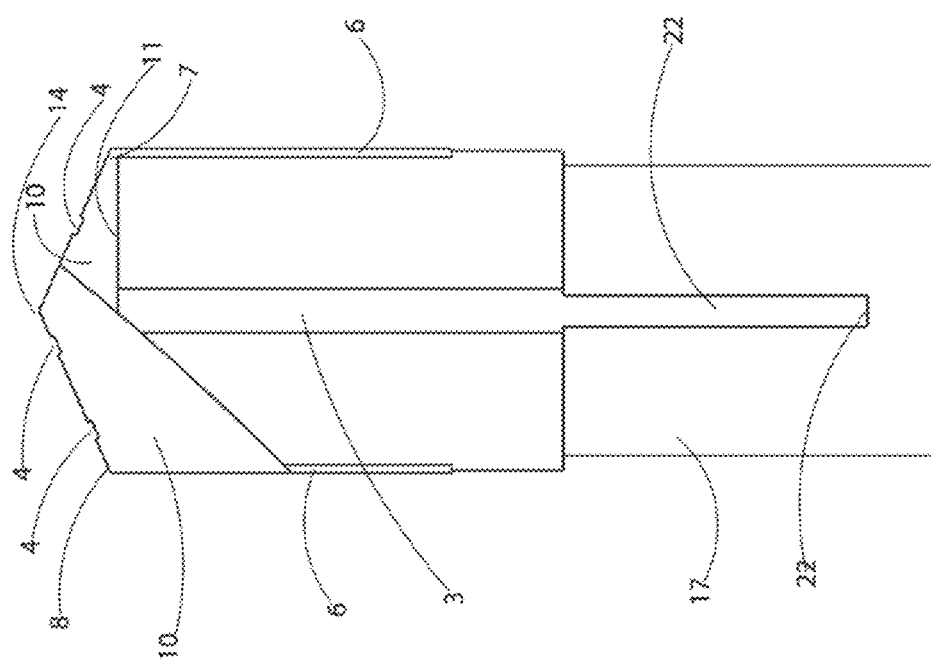
Figure 8A:
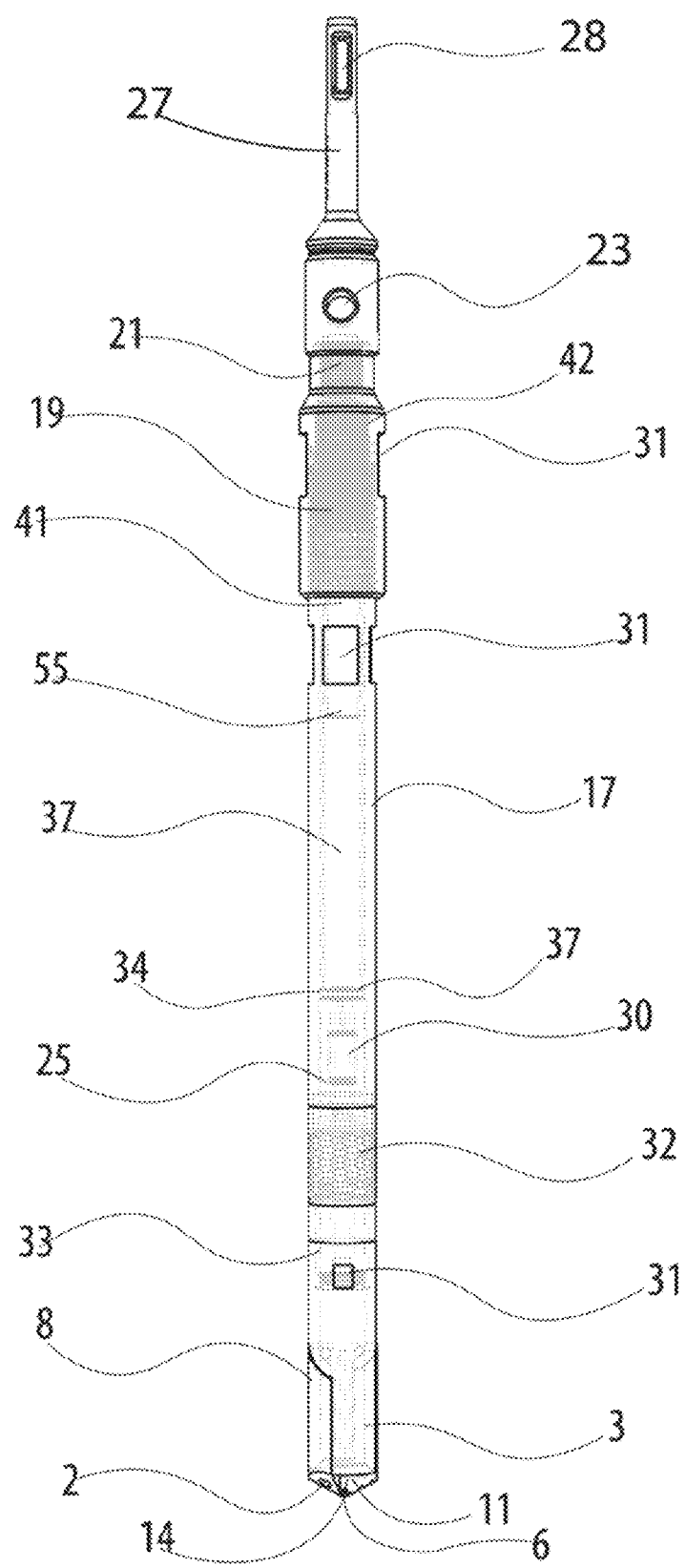
FIGS. 8A & 8B are schematic illustrations of side views of a 19 mm hollow tungsten carbide vacuumed metal sampling head in accordance with the present disclosure.
Figure 8B:
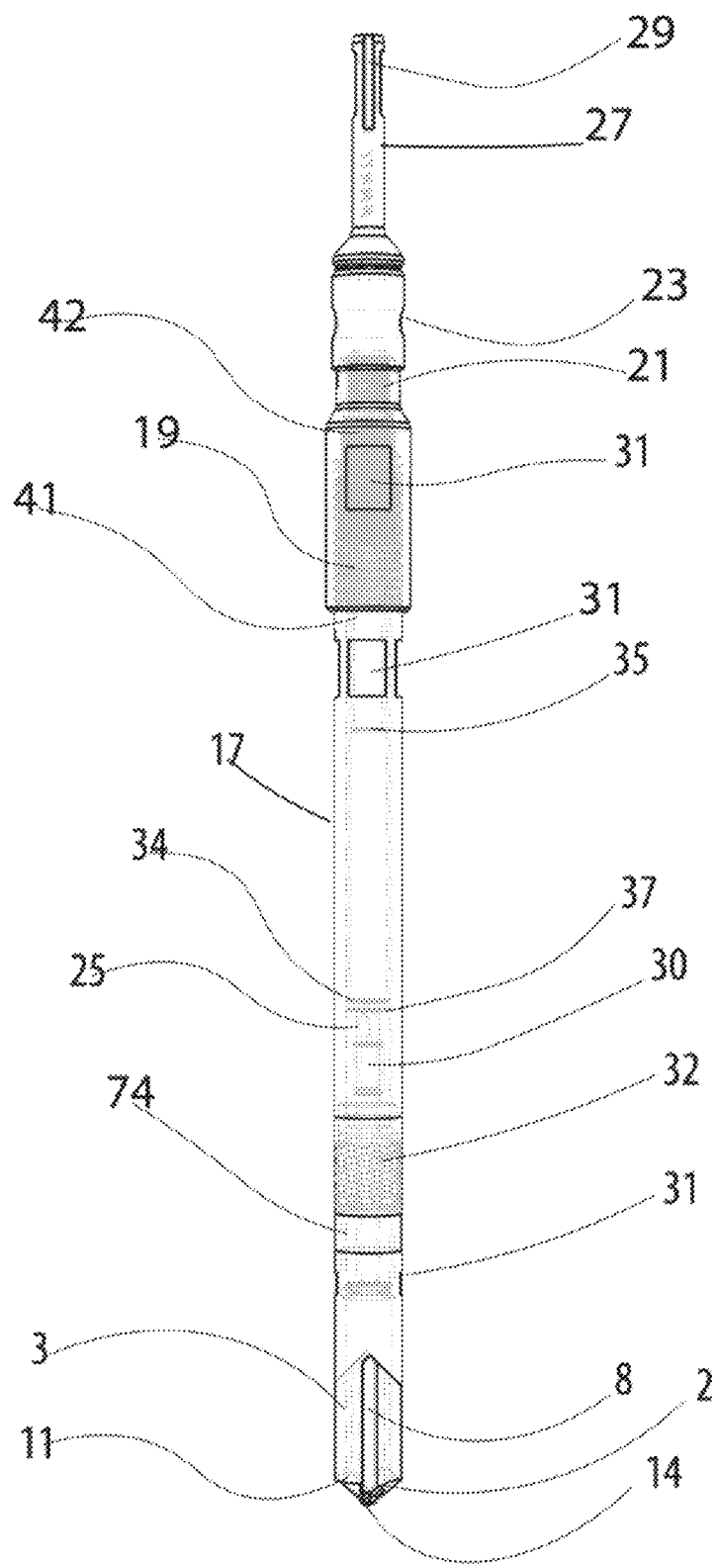

The third aspect of the disclosure provides a cutting sampling head 1 for a hollow drill bit 60 and will now be described in greater detail with reference to FIGS. 3, 4, 5, and 6. FIGS. 5 and 6 are close-ups of the front end of the hollow carbide metal sampling head. The hollow tungsten carbide sampling head has base chamfers on the contact edges of 45° at the tungsten carbide head base, as shown in FIG. 3. The chamfers enhance the brazing and fixing of the sample cutting head 1 robustly and securely into the sampling head holder FIG. 4, machined receiving mating surfaces for maximum surface contact and silver brazing material flow at the attachment point above 800 degrees Fahrenheit into the machine cut slots and along relief contact faces via capillary action flow between the two closely fitting components and fixing the non-ferrous tungsten carbide sampling head securely in position. The silver braze molten filler metal interacts with a thin layer of the base steel metal holder body, and when cooled, forms an exceptionally strong and airtight sealed joint becoming a sandwich of different metallurgically linked layers. The base face chamfers allow for a snug flush fit between contact surfaces, which vastly improves the tolerance and bonding of silver brazing strength and robustness, so no breakage is downhole. The sampling head holder's contact surfaces are angled radially to increase the surface area and configuration set, so there is no movement between parts; the carbide is precisely set centrally and cannot move in the radial cut seating slot. The sampling cutting head 1 ends of the cutting arm is may have end chamfers 8, which may be at a suitable angle of 45° to the base of the tungsten carbide sampling cutting head and the outer radial surface of the sampling head 1 as shown in FIG. 3 and FIG. 4. The side chamfers 8 prevent the binding of and the clogging of filings and chippings of the metal material at the sample cutting head. The metal component hole is cleared as the drill head rotates and allows for constant airflow and drill chipped metal alloy material clearance, allowing for easy retraction of the long metal sampling drill bit back out of the hole in the metal being penetrated and sampled. The apex T of the two-sampling head radial cutting arms 5 meet at a central high axial point of the sampling head 14. The apex forms a sharp point protruding from the tip, which allows a fixed drill start point on hard convex curved surfaces of zircaloy pressure tubes and also allows the centering and rate of feed into the metal surface to be more controlled, centered, true, straight penetration and reduced chance of breaking and shattering of the sampling head downhole on the surface sampled. The chamfered flat 8 surface changes to a large, curved surface 18 keeping the central point of the sampling head concentric to the cut wall surfaces so no wobble or chattering downhole occurs. Behind the radial cutting, arm edge is rake facets 3 divided into sections by chip grooves 4 spaced evenly across the cutting face and offset radially from the adjacent groove on the opposing cutting arm to give a staggered radial cut for each turn of the metal alloy sampling head. Each chip groove 4 is 0.02 inch wide and 0.02 inch deep with a 0.10 inch spacing between adjacent grooves spaced evenly across each of the cutting arms. One arm may have three chip grooves, the other two, which causes the metal surface to be cut and form chips or filings and metal dust in small particulate. Each of the chip grooves causes the previous cut surface to be chipped or filings and chippings into small enough particulate by slow drill bit feed through the metal, with the metal particulate, then funneled by the rapid vacuum airflow into the chamfered inlet 13 clearing the air and sample intake 11 in contact with the inner air passage of the drill tube body 17 preventing blockage by particulate sticking or build up in the narrow air inlet orifices.

The working cutting head has a thickness of 0.16 inches. The radius of the air-cooling holes is 0.05 inch to 0.25 inch depending on the sampling head diameter. The void angle between the cutting face edge and the rake edge's backside is 1100 or between 1050 and 115°. The chip breaker grooves 4 are offset by each other by 0.12 inch; each chip groove 4 is 0.03-inch-wide and 0.02 inches deep. The transition radius is 0.37 inches. The apex point angle is 1250 and maybe between 120° and 130°. The angle from the cutting-edge sample face to the rake face is 40° and allows for the clearance of drill chips and filings and chippings as the sampling head is rotated and can be between 350 and 45°.

The length of the hollow carbide body cutting head is 1.0 to 1.7 inches with a sampling head diameter of 0.75 inches. The chamfered flat 8 is 0.1 inches. The slot machined into the steel holder is 1.40-inch-deep and 0.16 inch wide. These are machined and cleaned to very high tolerances to allow a snug tight fit of the tungsten carbide hollow sampling head. The shank diameter is 0.73 inch with a 0.02-inch clearance gap to the 0.75-inch diameter head to allow airflow to and through tungsten carbide sampling head 1. The carbide holder's internal diameter is 0.5 inch and allows the unimpeded flow without blockage of the metal filings and chippings of activated metal incremental discrete sample collected. The drill bit point distance to the air particulate guide front edge forms a 3 mm clearance, which is paramount in allowing immediate clearance of all filings and metal dust in the horizontal or angled sampling profile directions. The metal cutting with complete sample removal and capture prevents the loss and dispersal of metal filing samples dropping away from the sampling head air particulate front end orifices and air guide inlets. This head configuration of cutting arms and air inlet orifices are crucial in preventing the drill bit from snagging and sticking down the deep hole while drilling and sampling the activated metal. Sampling is all done without liquid coolant, which would spread radioactive contamination, only using dry air under 27 inches of mercury vacuum force, preventing drill bit blockage, and allowing activated metal sample retrieval. The particulate air grooves are 1.33 inch-long and 0.25 inch wide, and the inner end edge is chamfered at 45° to create a funnel edge to guide the airflow into the end of the drill bit and guides the chips and filings toward the center of the airflow vacuum passage. The end of the air guides sits only 3 mm behind the drill apex and sits lower than the sampling head cutting edge and thus allows airflow and the collection of all filings and chippings away from the front end of the sampling head immediately. All material is retrieved as it is cut from the hole in the metal alloy component being sampled inside the nuclear reactor core. The diameter of the sampling head can be 38 mm to 11.11 mm.

FIGS. 5 and 6 show the sampling cutting head 1 of the invention comprising two cutting arms 5 each of the same configurations are 180 degrees directly opposed. The cutting edge 7 extends in a straight line from the central axial point 14 to the outermost radius of the sampling head cutting edge 7. A side chamfer 8 extends backward axially parallel to the sampling head cutting edges from the cutting edge having a perpendicular angle of 90° to 45° to the cutting edge face 7 forming a flat on the sidearm 5, which reduces the contact surface area of the drill bit sampling head-turning against the hole cut metal surface thus reducing the drilling and rotational forces by preventing cut drill debris binding of the head in the hole and the sampling head chattering and jumping down the deep hole due to debris jamming the smooth rotational cut through the metal alloy material being sampled. The hollow drill bit 60 has a cylindrical hollow tubular sampling head 1 and drill tube body 17 comprising a hollow cylindrical cavity space extending the length of the body of the drill bit. The drill bit's back-end shank is machined to connect and couple to the drill quick-connect collar and air adapter 66. When the drill bit and air adapter are coupled, the air and metal sample flow through the hollow central cavity space with minimal contact surfaces and smooth interior cavity walls to prevent metal filings and chips from sticking and clumping in the air adapter internals while passing through to the hollow vacuum connection line 70. The 19 mm metal sampling head 1 can be of 38 mm diameter for drilling of deep narrow holes of 38 mm to 10 mm diameter and with the retrieval of all of the cut metal filings and alloy chippings of metal sample material from the bottom of the hole is assisted by the provision of a hollow one-piece solid tungsten carbide cutting body 1 set 3 mm forward of the tool holder tip of the particulate air guides 15 to maximize airflow around and through the hollow tungsten carbide head so clearing metal filings and dust as activation product metal sample away from the sampling head cutting edge 5 and from the self-centering central axial point 14 inwards through the central air passage 17 via air inlet 11 connecting the front of the drill bit to back up to the hollow shank 24 extended out from up to 25 cm to 7-meters. The drill bit instantly seizes up, ceasing the turning and cutting if grabbed and blocked with uncleared metal sample debris filings and dust and is grabbed in the metal hole being sampled if no airflow or vacuum is present, so every air orifice, air guide, and clearance air inlet 11 are critical for sampling retrieval and deeper sampling progress. The sampling head configuration is a culmination of evolution in reinforcing brazing and extension of the particulate air guides and cutting edges optimized and robust enough to survive dry metal drilling with total sample retrieval and capture. A vibratory device causes vibration from shank down the drill bit to sampling head tip 1 and vibrates and dislodges any blocked or backed up metal filings, chippings, and metal dust sampling debris. The front material head parts of the hardened heat treated slot for the sample head are axially set back 3 mm from the main hard hollow tungsten carbide sampling head 1 and radially set back from the outer diameter particulate air guide supports 15 that are swept by the termini of the two cutting arms 5 on the head of the hard hollow tungsten carbide sampling head. The robust hollow sampling cutting head may be press-formed, ground, and machined from one piece of tungsten carbide with the flank, height of point, outer corner, taper shank, tang, straight shank with tang, cutting edge, margin, margin width, land width ground cutting edges and faces made using any known method for forming said parts from said material. The shape of the sampling head positively affects airflow and metal chip and metal filing pickup efficiency when sampling horizontally or at an inclined angle with the removal of particulate and filings from the radial cutting arms 5 instantly.

An alternate embodiment for 11.11 mm or smaller outer diameter with similar functionality by physically keeping the air inlets free of brazing material that forms a high meniscus and when cooled, beading of the braze meniscus at the joint interfaces restricts the hole thus causing clogs of the sample at the end of the drill bit air intakes. In FIG. 7, plan and side views of one embodiment of the 11.11 mm hollow tungsten carbide vacuumed metal alloy sampling head, the drill bit head comprises a carbide blank insert of diameter 0.44 inches or 11.11 mm with chipping grooves behind the cutting edge. In the tube holder, slanted air grooves allow all particulates to be collected on drill bit touchdown on a sampled metal surface. Air grooves run the drill bit shank's length to allow air to the front end of the sampling head insert 10 when buried deep in the metal sampled. This airflow from the shank guarantees chip and metal filings and chippings removal from the drill bit's front end, preventing clogging and blocking the air holes and guides. The carbide back edge that seats it in the holder has 45° chamfers to allow for a solid, robust attachment via vacuum silver braze flow into the contact seating surfaces. The shape of the sampling head governs the cutting-edge durability and lifecycle of the cutting edges 7 to hold the tungsten carbide securely during the intense heat generated during dry drilling; no lubricant or drilling fluid is used, just air under vacuum. The disclosed invention maximizes the relative area size of the air inlet sections while maximizing the physical integrity and dimensions of the air particulate guides wall thickness and the bifurcated slots within which the hollow carbide sampling head sits securely, rigidly held by the vacuum silver brazing applied to the contact ferrous and non-ferrous surfaces. The relative surface area of the air inlets is 50% by drill bit front end surface area and not less than 20% to maximize airflow into and through the drill tube body 17 of the metal filings, and metal chips flow for metal chip and metal filing removal purposes, and the cooling and the clearing away of metal sample particulate from the cutting surfaces to then proceed to greater depths. The flat 8 running along the outer edge and perpendicular to the nuclear drill metal sampling head allows the inflow of air between the hole cut surface and the tungsten carbide body. About 10% of the air volume flows through this relief aperture/gap, clearing the metal particulate and filings and metal chips away from this rotating surface, allowing the drill bit sampling head to turn and prevent binding of the sampling head in the cut metal hole. The common air passage 11 through the drill tube body 17 begins at orifice 2 and air passage inlet 11, as shown in FIG. 5, of a plan view of a 19 mm hollow tungsten carbide vacuumed metal sampling head in accordance with the present disclosure. The rapid movement of the metal particulate and air at the activated steel layer and the metal sampling head interface is critical to the function and incremental depth progress so allowing the clearance of cut chip and filing metal particulate and dust which prevents excessive overheating and expansion of the sampling head to bind in the cut hole. The rapid stream of cold air over the sampling head surfaces, relief edges and through the orifices 2 and within the air inlet particulate guides 15, along the outer surface of the air particulate guides 15, the outer edge 8, and the outer cutting edge 7 and the cutting arms 5. The gap 6 between the hollow carbide outer diameter being slightly greater than the drill tube body 17 so that the upper chamfered edges 15, 13, and 12 remain unworn and untouched by the drilling cutting forces, keeping the silver brazing and contact surfaces intact, so there is no degradation of the steel body holder, the sampling head does not disintegrate with the rotational drilling and cutting forces through the hard activated metal alloy.

It should be clearly understood that while the invention has been described in conjunction with specific embodiments thereof, it is apparent that many alternatives may be derived. Accordingly, it is intended to embrace all such alternatives and embodiments, modifications, and variations that fall within the scope of the claims. Modifications and variations will be apparent to those skilled in the art. As shown in FIGS. 7a, 7b, 7c, and 7d, the metal cutting sampling head has instead of the bifoil cylindrical hollow carbide sampling head 1 a simple robust insert 10 which is generally flat and has two cutting edges of zero rake angle with chip grooves 4 as described in the previous typical embodiment and in addition to the cutting insert 10 the drill bit 60 may have air inlets 11 with features and axial running air grooves 9 that are integral air channels with the steel tool holder hollow shank body and also with the semicircular in cross section grooves running straight and parallel to the axis of the drill of at least 1.5 mm round cross sectional area forming groove 22 extending and running partially up the body up to 5 cm behind the sampling head so that in drilling deep metal, air still flows to the drill bit tip 14 up to angled ground cutaway sections 35 and 36, increasing the opening size of air inlet 11 by angling down and sweeping back to the outside wall radius increasing durability and to prevent seizure and binding of the metal sampling head down the deep hole, but can also be a super V-groove or a square slot groove that allows air to flow in towards the drill bit tip 14 with air inlets 11. The rapid airflow of 96 CFM at 27" Hg vacuum force moves along these two radially opposed air grooves 9 and also between the cut wall surface and slightly narrower drill tube body 17 which has a wider gap 6 keeping the sampling head and cut metal surface cool and allowing the clearance and retrieval of filings and metal chips and metal powder back along and through the one common and united airway 11 of the sampling cutting insert 10 and the hollow drill tube body 17. Two max-V air particulate air grooves in cross-section are congruent diagonally opposed twofold dual triangles. As shown in FIGS. 7a, 7b, 7c, and 7d, a first groove relief is configured to be at right angles to the cutting edge 7 insert and has a second air groove relief opposite the first air groove relief of the drill bit metal sampling insert 10. The two air grooves 9 are in communication with the air and particulate inlets 16 of the metal sampling insert 10.

During sampling operations, the activated metal component is cut and sampled by the tungsten carbide sampling head insert cutting edges 33, whereby metal chips and metal filings and dust are formed and are pulled under vacuum through the central cavity space of the sampling head. The air groove reliefs, the air particulate air guides, inlets, and cavity internal diameter are idealized to maximize airflow through the tip to prevent blockage of the sample in the interior hollow carbide cavity space. Thus, allowing the metal filings and chips to be rapidly removed and retrieved under vacuum and avoiding drill bit blockage and binding through seizure in the cut metal hole. The proximal end of the two opposed air particulate guide inlets 11 have rounded, and chamfered edges 13 and 12, which prevents localized clumping and clogging of the inlets by the cut and sampled metal as chips and filings in formation, air moving over the rounded edges displaces the filings and chips before the chance of a blockage occurs. The rounded and chamfered edges decrease the filings and chips' chances of becoming static and stuck, and all inner surfaces are machined smooth to prevent filings and chips from sticking and improving the chip filing airflow. Each air grooves 9, and air particulate guide 15 run straight and parallel to the axis of the metal sampling head insert 10 and have a generally rectangular groove cross-section. This chip and filing collection without clumping and blockage is reliably cleared by no sharp angular edges or snag points, or high braze meniscus at contact surfaces and edges. The hollow metal cutting sampling head is also more reliably cleared of cut metal with increased vacuum and airflow through the air inlets, particulate air guides 15 with chamfered reliefs 13 and 12 causing the drilled metal particulate and metal dust to be funneled towards the air inlets 11 and air holes 2, after which, at the cutting edges, 7 metal filings and metal chip and metal filing and dust pickup occur at the front end of the metal sampling head 1 by the rapid flowing vacuum airstream towards the drill tip air inlets and particulate air guides. Accordingly, as the air stream enters the inlet reliefs area adjacent to the cutting edges 7, the air interacts and picks up the metal chips and metal filings and metal dust, entraining them in the air stream negating plug formation on the rake facet 3 and drawing them away into the central shared air passage 11 and 16, adjacent to the cutting edges 7 and cutting arms 5.

The carbide insert is 0.11-inch-thick and 0.56-inch-long and sits in a machined cut slot 0.11 inch, and 0.45-inch-deep with 45° chamfers on the mating braze faces. The carbide head's apex is 0.11 inch above the air filings and chippings entry hole end face, ensuring the collection of all cut metal filings and chippings material. The air grooves of radius 0.03 inch run 1 inch along the steel shank of diameter 0.44 inch and the wall thickness of 0.11 inch. An angled cut of the tube holder downward 45° swept across the carbide cutter allows maximum size aperture for airflow and prevents the hole's blockage by ensuring the chips and metal filings and chippings are cleared from the rotating cutting sampling head edge. The vacuum air passage's internal diameter is 0.28 inches with an outer diameter of 0.39 inches, thus allowing an air clearance gap for the rapid movement of air at 96 CFM through the two orifice holes directly behind the cutting edges 7. A vacuum force is continuously applied to reduce the chances of plugging and blockage, as air flows downhole between hole wall and drill tube body wall 17 around the inflow air channels at the cutting head edges and into air inlets 11 and air holes 2 channels via particulate air guides 15 with the cut and filings and chippings and powdered and metal dust material inflow of air and metal particulate at depths of up to 7.0 m with forward pressing rotational cutting force and slow feed rate penetrating hard metal alloy layers and void spaces.

The metal sampling equipment, sampling gantry, and component assembly are anchored to the reactor bioshield wall in one embodiment. The sampling operations are in the horizontal direction to facilitate representative samples from the different locations and depths in the CANDU heavy water reactor inner metal activated components. In FIG. 1, the invention's embodiment is classically exemplified when sampling through the nuclear reactor bioshield and nuclear reactor core calandria metal alloy activated internals. Each incremental depth of sample from each sampling access hole is captured and contained individually and continuously in an incremental manner. As hard metal alloy samples are retrieved, they are instantaneously screened for sample activation product total dose using calibrated handheld radiometric instruments.

The sampling profile entry point is precisely defined by identifying the first sampling location and measuring with a metal tape measure from the reactor centerline 101. The percussion drill adapter mechanism 38 is positioned onto the sliding carriage plate top 61 and locked into position using lock-off O-rings 62. The rail O-ring clamps are secured so that the drilling mechanism and 50 cm masonry drill bit just contact the sampling location marked on the wall. The hole's position is selected close to the reactor centerline 101 for maximum neutron flux and worst-case activated sample scenario. The angle of the sampling gantry 50 can be between 5 degrees and 20 degrees. At the NPD reactor, the adjusted angle of declination of 10 degrees was set with an inclinometer precision of 0.5° and locked off, so it was static. A hole is drilled through the concrete wall to the required depth to allow drill bit longer lengths access. A 75 cm threaded end extension is used to extend the drill bits to the required cutting and sampling depth in confined working areas not suitable for continuous length hollow drill bits. After each concrete increment, the filter is changed to prevent cross-contamination and any reduction in airflow to the sampling head. Filter change out achieved by pressing in and unscrewing the bayonet fitting holding the filter housing to the manifold and unscrewing the filter from the housing before carefully dispensing the sample into a suitably labeled sealed preweighed container. To ensure the absence of cross-contamination between consecutive samples, the entire sampling circuit is replaced between each consecutive incremental reactor core metal alloy sampling operation.

FIG. 2 represents the drill bit penetrating through the ilmenite concrete bioshield wall 180, missing all 6 layers of rebar 51 before penetrating the mild steel vault liner 170 at 2210 mm to 2217 mm. The reactor vault void space of 903 mm is traversed to contact the aluminum calandria outer 160 at 3120 mm to 3142 mm. The calandria outer shell void space 150 of 650 mm is traversed, making contact with the aluminum inner calandria wall 140 at 3792 mm and penetrating at 3799 mm before traversing the 1001 mm void space across the reactor calandria to make contact with the aluminum calandria tube 130 at 4800 mm and penetrated at 4802 mm. A camera is inserted into the aluminum calandria tube wall 130 hole into the zircaloy 2 pressure tube using a 5.5 mm ID video borescope 90. One 4 mm outer pressure tube Zircaloy sample is retrieved from a depth of 4807-4811 mm, and one 4 mm inner pressure tube Zircaloy sample 102 was retrieved from a depth of 4896-4990 mm. During activated pressure tube sampling, the drill bit sampling head traversed the 5 mm void space between adjacent wall interfaces, and the filings and chippings of metal alloy nuclear-activated sample material are collected in the sample filter. Inert gas is incorporated into the sample retrieval and a functioning flash arrester into the sample collection process to mitigate any flash occurrence of the pyrophoric Zircaloy filings and chippings. The invention disclosed also confirms that there were no aluminum dummy fuel bundles present as they are not encountered by the drill bit traversing the entire 85 mm tube inner diameter without interference. A borescope 90 and mini probe 5.5 mm camera 93 is placed down the hole, and photographs taken of the zircaloy 2 pressure tube 102 penetration and calandria sample entry holes. Table 1 shows a summary of all materials sampled and collected, and Table 2 shows the time to penetrate each material. The reactor drill bit sampling head after clearance and collection of samples pierced the opposite inner concave surface of the zircaloy 2 tube with an obtuse glancing 60 rpm cut high above the calandria tube diameter. The successful sampling and characterization results using the TruProBit® invention are shown in Tables 3 and 4. uncertainties in the calculated theoretical neutron flux model are highlighted and negated using actual samples to calculate the real activation product activation radiological activities. The actual sample activation product characterization data is then compared to the theoretical activation model. The worst-case activation summation allows the modelers to readjust their activation modeling calculations to prove to the national nuclear regulators that radioactive waste acceptance criteria and process removal toward final nuclear power plant site delicensing.

TABLE 1

Hole 1 Total Activity Bq/g

| Sample # | Matrix | Total Alpha/ Beta Bq/g | Total Gamma Bq/g | Total Bq/g |
|---|---|---|---|---|
| 1-23 | Concrete | 6.98E+03 | 1.61E+03 | 8.58E+03 |
| 24 | Mild steel liner | 1.27E+03 | 6.82E+02 | 1.96E+03 |
| 25 | Aluminum | 7.99E+01 | 5.46E+01 | 1.35E+02 |
| 26 | Aluminum | 1.07E+05 | 2.18E+04 | 1.29E+05 |
| 27 | Aluminum | 2.37E+05 | 6.84E+04 | 3.05E+05 |
| 28 | Zircaloy | 4.22E+05 | 8.33E+04 | 5.05E+05 |
| 29 | Zircaloy | 1.91E+06 | 1.04E+05 | 2.02E+06 |
|  |  | 2.69E+06 | 2.79E+05 | 2.97E+06 |

TABLE 2

Approximate Dry Sampling Retrieval Time

| Material | Depth | Sampling time Minutes |
|---|---|---|
| Concrete | 23 @ 100 mm each -2210 mm | 120 |
| Mild Steel | 1 @ 7 mm each 2210-2217 | 20 |
| Black Steel | 50 mm | 80 |
| Calandria ALCAN C54S-0 Outer | 1 @ 22 mm each 3120-3142 mm | 40 |
| Calandria ALCAN C54S-0 Timer | 1 @ 7 mm each 3792-3799 mm | 15 |
| Calandria Tube Aluminum | 1 @ 2 mm each 4800-4802 mm | 1 |
| Lead | 100 mm | 90 |
| Boral Sheet | 6 mm | 150 |
| Stainless Steel 316 | 5 mm | 40 |
| Stainless Steel 301 | 5 mm | 40 |
| Graphite | 60 cm | 15 |
| Tungsten Tile | 5 mm | 120 |
| Reactor Inner Zircaloy2 Pressure Tubes | 4 mm | 5 |

TABLE 3

Vandellós Unit 1 Reactor Core Metal Corset Samples Total Tritium and Gamma Activity Bq/g

| Sample# | Matrix | Total Depth cm | Total Tritium Bq/g | Total Gamma Bq/g |
|---|---|---|---|---|
| 3 | Carbon Steel | 628-632 | 1.47E+01 | 1.19E+03 |
| 9 | Carbon Steel | 632-634 | 3.38E+00 | 3.49E+03 |
| 10 | Carbon Steel | 634-636 | 0.00E+00 | 3.23E+03 |

Figure 10:
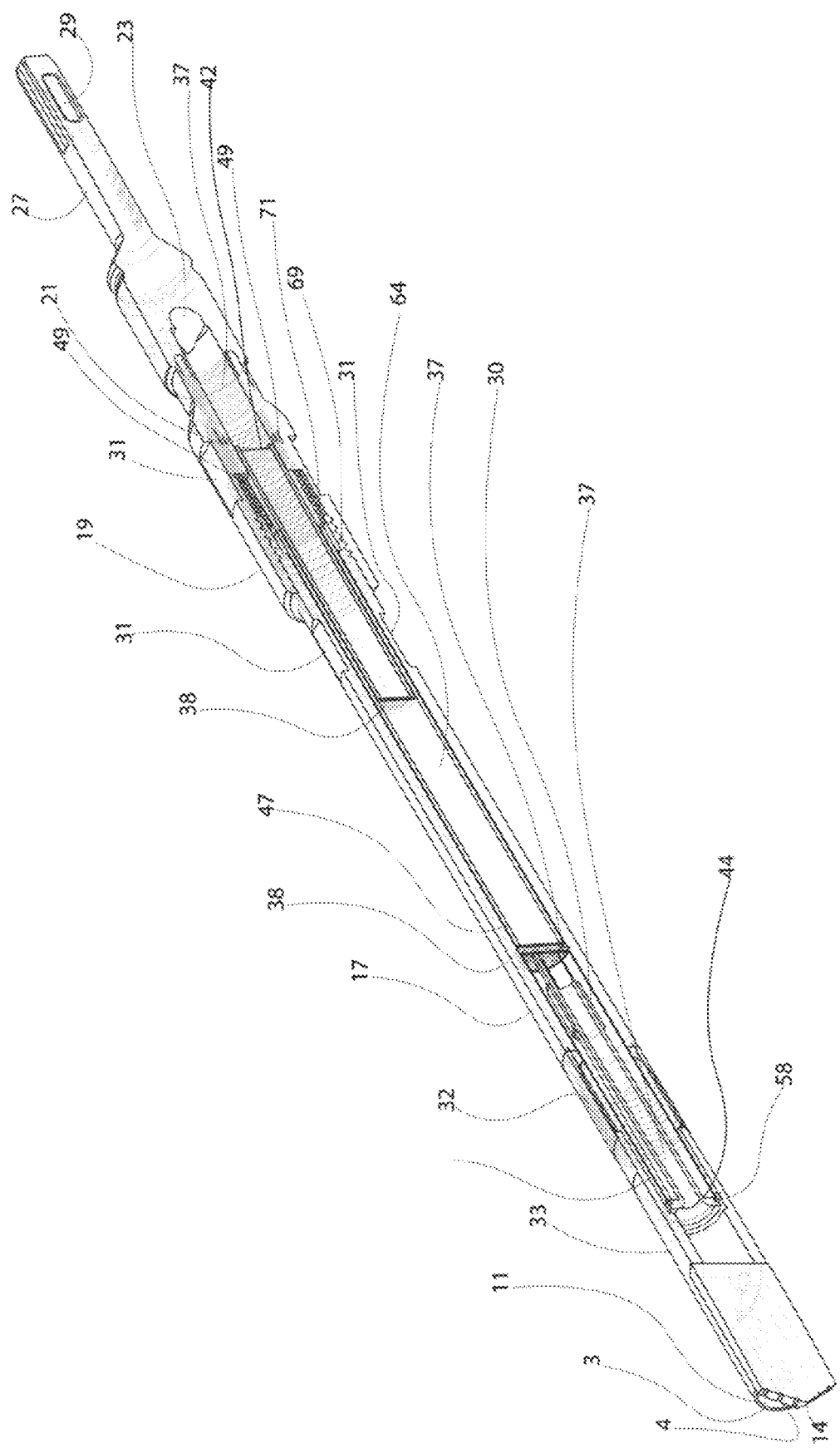
FIG. 10 is a schematic illustration of an orthogonal cutaway view showing the internal configuration of 19 mm hollow tungsten carbide vacuumed metal sampling head in accordance with the present disclosure.
Figure 11B:
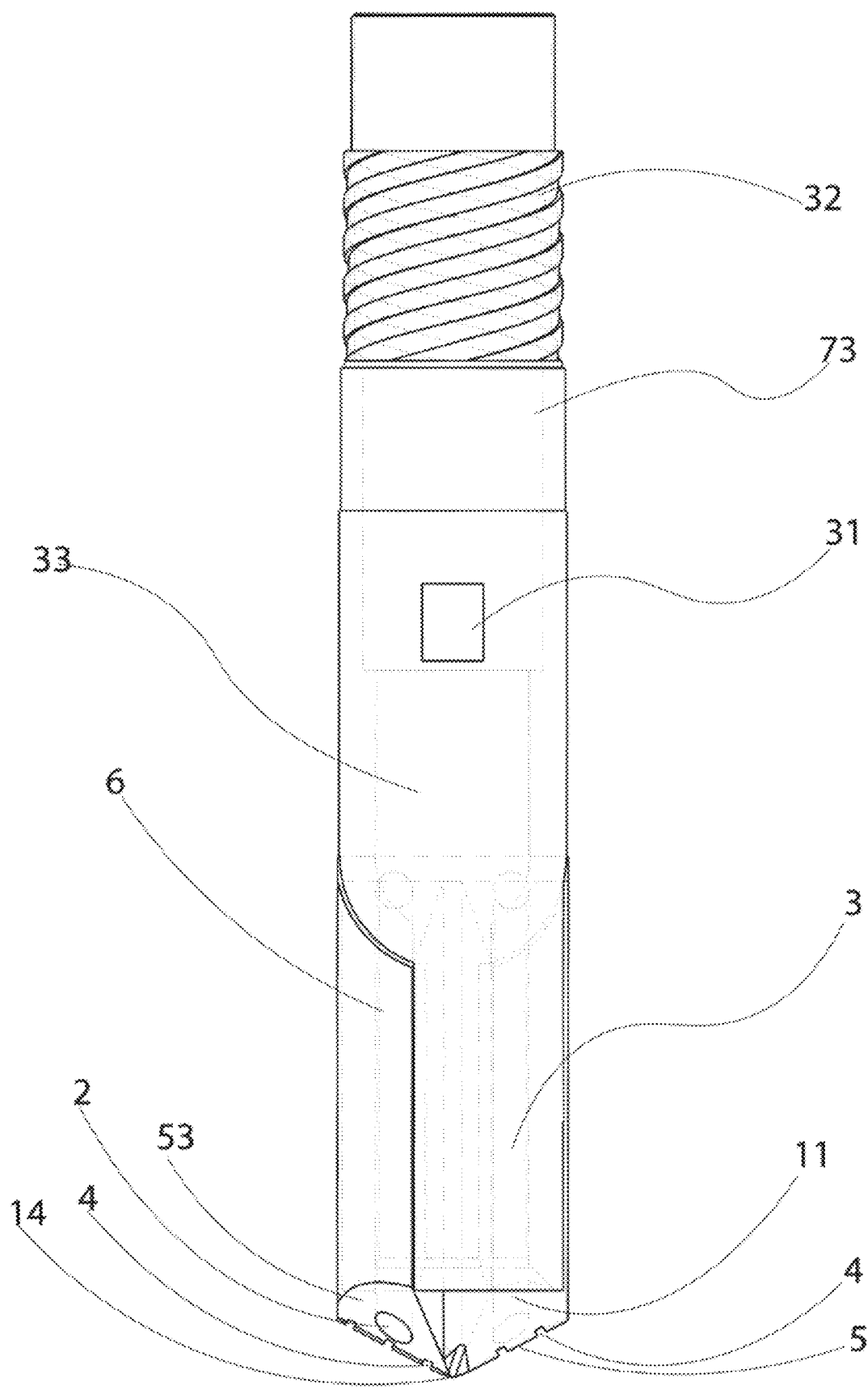

Referring now to the side view drawings, FIGS. 11a & 11b of the metal sampling head, whereas the configuration exemplifies an embodiment of the tungsten carbide hollow sampling head 1 and drill bit 60 of the present invention. The present invention provides a replaceable hollow sampling cutting head tool in accordance with the embodiment of the invention. The hollow sampling head gets worn, and sharpening is required, but the replaceable sampling head of the used drill must be discarded or replaced with a new sharp sampling head 1 with helical thread attachment cutting tool insert in accordance with the invention. The replaceable screw-threaded TruProBit® sampling drill bit head 1 as shown in FIGS. 9, 10, 11a, and 11b, an orthogonal cutaway view showing an internal configuration of 19 mm hollow tungsten carbide vacuumed metal sampling head in accordance with the present disclosure, has as previously described in embodiment 1 of the present invention the same edges, reliefs and sampling head configuration as previously described in FIGS. 3, 4, 5 and 6.

Wherein the replaceable hollow sampling cutting head of the drill bit 60, having a replaceable cutting tool head 1 at one end and rigidly fixed at its rear end via 4 square thread helical male screw threads forming a quadruple helix of pitch angle 7 degrees, or between 2 and 8 degrees to guarantee concentricity and alignment. The tightness of screw lockdown is maintained and with ease be able to unscrew in one revolution even when the metal cutting sampling head is subjected to extreme torque when buried deep in the activated metal component sampled, using clamping flats 31 to hold static while unscrewed from its receiving square thread female threads of the drill tube body 17. The locking angle is the same as the helix angle as of the quad threads whose pitch angle is no more than 8 degrees as the replaceable metal sampling head becomes loose as rotated. The threads tighten in one revolution of the head 1 onto the hollow tube body 17 receiving the hollow 4 helical square threaded female threads of matching pitch 32 at the forward end, concentric with cylindrical stainless steel primary tritium trap cartridge wall 47 and locking off on the shoulder 73 with very tight tolerances between threads and the counterbored threading of the drill tube body 17 avoids sampling head wobble, kickback, and inaccurate concentric hole alignment. The sampling head section may be extracted from the metal being sampled and penetrated. It is easily unscrewed and replaceable while being robust, sturdy, and strong to convey the rotational and drilling cutting forces or if inadvertent sampling head snags with a four helical thread joint having a wall thickness of the drill tube body wall 17 at least twice the depth of the helical thread. The sampling head 1 is easily detached, so when the tip cutting edge portion becomes worn and ground down and no longer produces sample due to blunt edges, only the sampling head needs to be replaced, the body of the drill is unaffected by drilling operations and can be reused without being replaced. The replaceable screw-threaded hollow tungsten carbide sampling head may be easily sharpened by precision grinding rather than cumbersome grinding in handling, and holding static grinding angles for very long drill bit lengths up to 6.5 m is imprecise. This detachable sampling head reduces costs and radwaste volumes, prevents cross-contamination between consecutive incremental sample acquisition, and allows for further depth of metal sampling.

Figure 9:
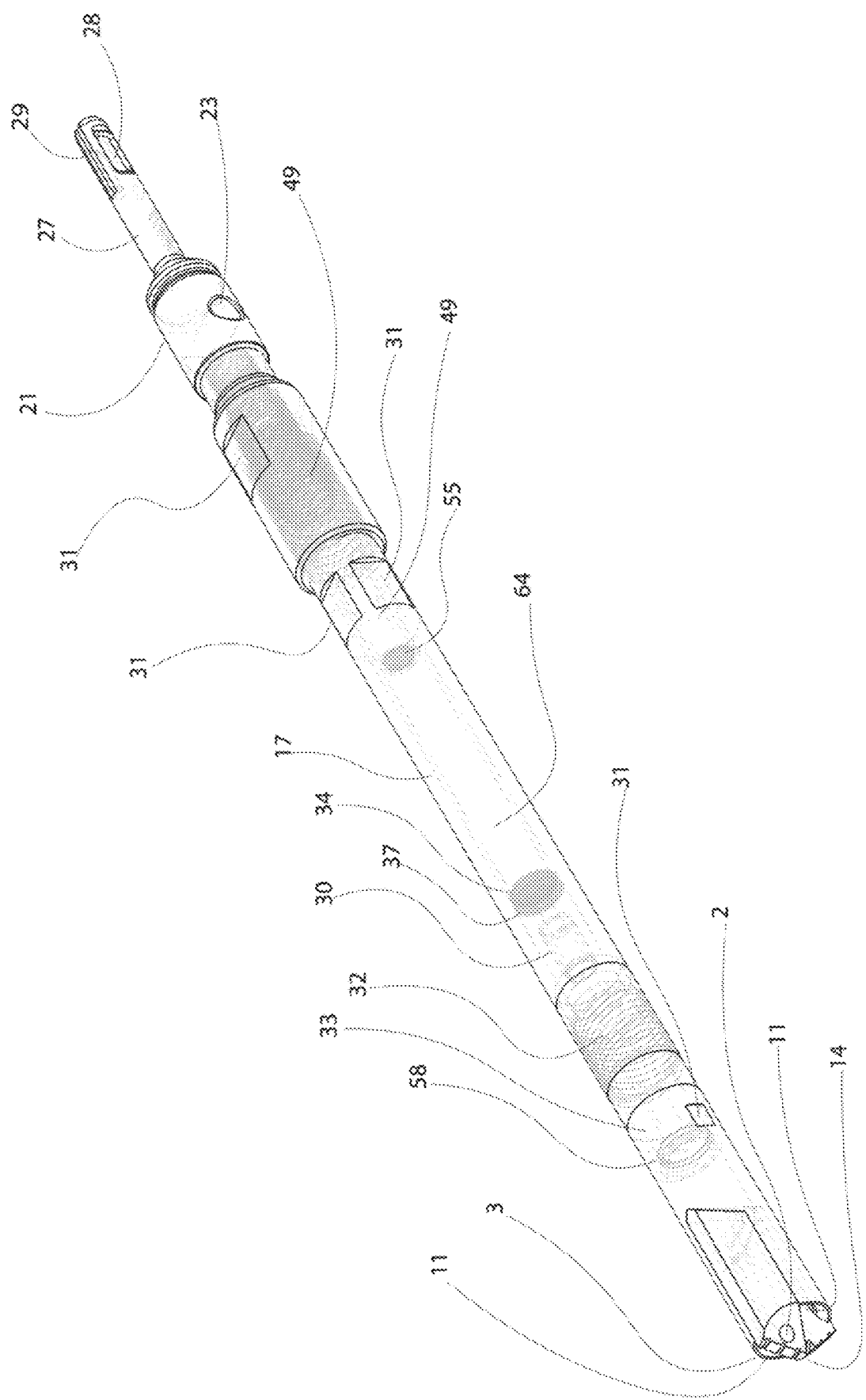
FIG. 9 is a schematic illustration of an orthogonal view showing the internal configuration of 19 mm hollow tungsten carbide vacuumed metal sampling head in accordance with the present disclosure.

FIGS. 9 and 10 of the embodiment comprises a slow feed of cut as the tungsten carbide sampling head rotates and cuts and chips the previous cutting edge sampled material, collecting the metal filings and chippings and fine metal dust during the drilling by using a self-centering specialized tungsten carbide cutting hollow vacuumed sampling head with a continuous vacuum force wherein the retrieval and collecting comprises creating airflow and vacuum to move the activated metal filings and chippings and activated fine metal particulate through a flow passage within the drill bit such that the filings and chippings contact a first filtration device in hermetic communication with the flow passage contained within a sample filter cartridge. A variable diameter shank fitting is utilized to receive screw-threaded variable diameters of hollow shank 19. The shank head shoulder lock and unlock flats 31 help grip tighten and loosen the quad helical threaded coupling. The air groove round bottom high point terminus 26, allows air to be drawn into the cut metal hole and the filings captured in a particulate trap 37. with recessed front face below the height of the cutting edge 7, angled cut air inlet facet 30. The tungsten carbide sampling head 1 is vacuum brazed into the machined heat hardened 4130 steel adapters to hold the tungsten carbide sampling head securely and prevent loss inside the nuclear reactor due to drill braze failure. The cutting edges have 5 chip breakers 4 cut into the cutting faces, 3 chip breakers on one side, and two chip breakers on the other side of the cutting faces of the sampling head and offset from each other to guarantee metal cut material down the hole is chipped off by the offset chip breaker on the following sample head following cutting face every half a revolution. A front-end 0.5 µm stainless steel screen mesh 37 allows only the vacuumed air stream to pass, with the metal filings and metal dust captured and contained in the particulate inlet funnel 37. The cylindrical stainless steel primary tritium trap cartridge wall 34 has a secondary 0.5 µm stainless steel screen mesh 55, and a secondary charcoal tritium trap stainless steel cartridge wall 41, secured in position by the threaded shank coupling 19, with the threaded stainless steel outlet cap 21, with a backend 0.5 µm stainless steel screen mesh 42. An O-ring particulate filings/chips funnel seal 58 creates a hermetic seal. The tang longitudinal groove coupling to drill motor 29. The metal filings, metal chip/metal dust particulate funnel 44, is positioned before the primary charcoal tritium trap matrix 64, with the shank screw threaded coupling 69, screwed tight to hold the central tritium capture cartridge static and in contact with the cylindrical stainless steel primary tritium trap cartridge wall 47, held by the mechanical screw shank inner shoulder compression point 71 via the cap screw inner shank coupling threads 49. This embodiment enables one to collect the sample in a cartridge built into the drill tube body 17.

Figure 12:
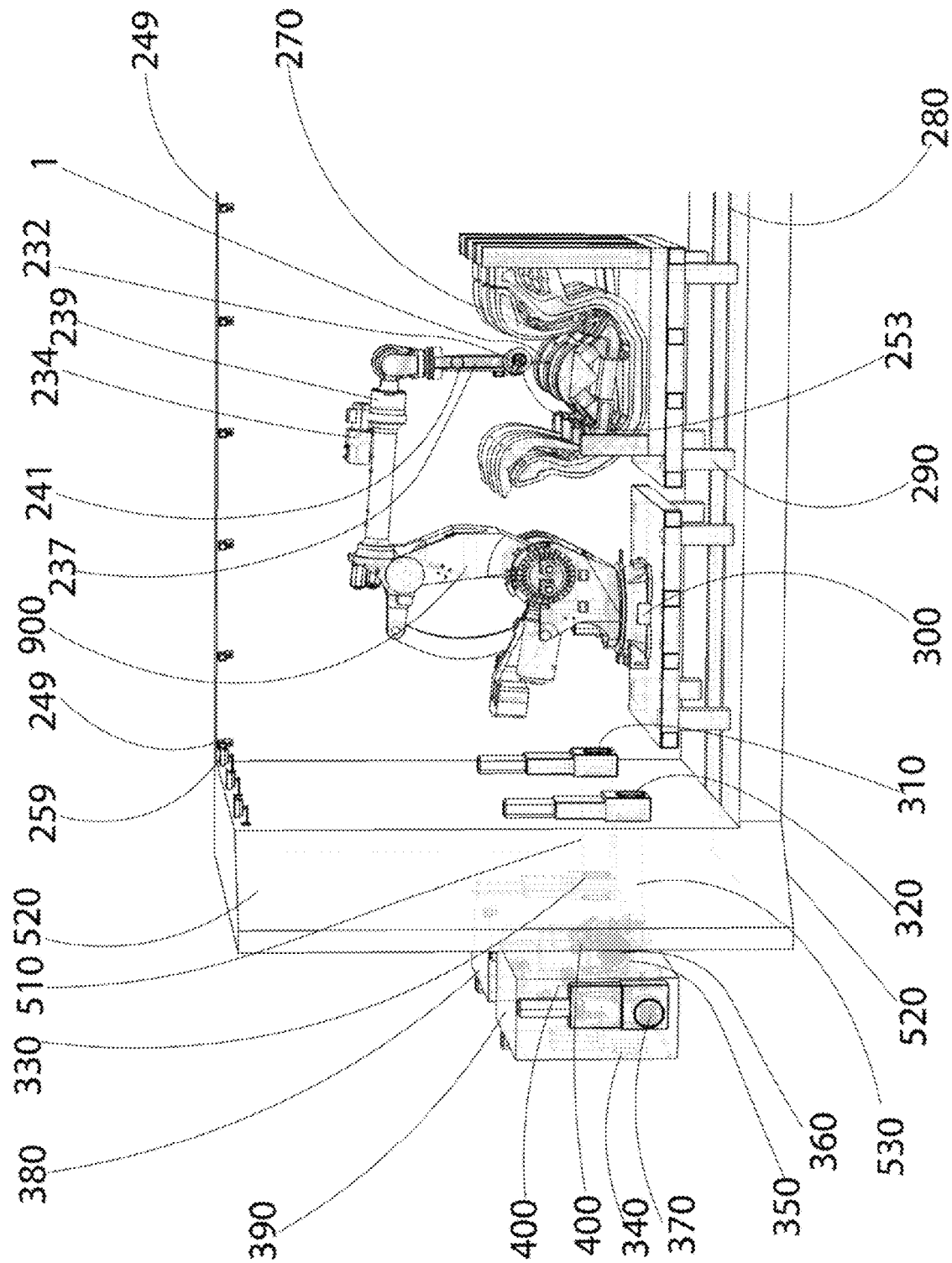
FIG. 12 is a schematic illustration of a side view cutaway of remote handled hot cell robot activated component sampling & characterization station using a 19 mm hollow tungsten carbide vacuumed metal sampling head in accordance with the present disclosure.
Figure 13:
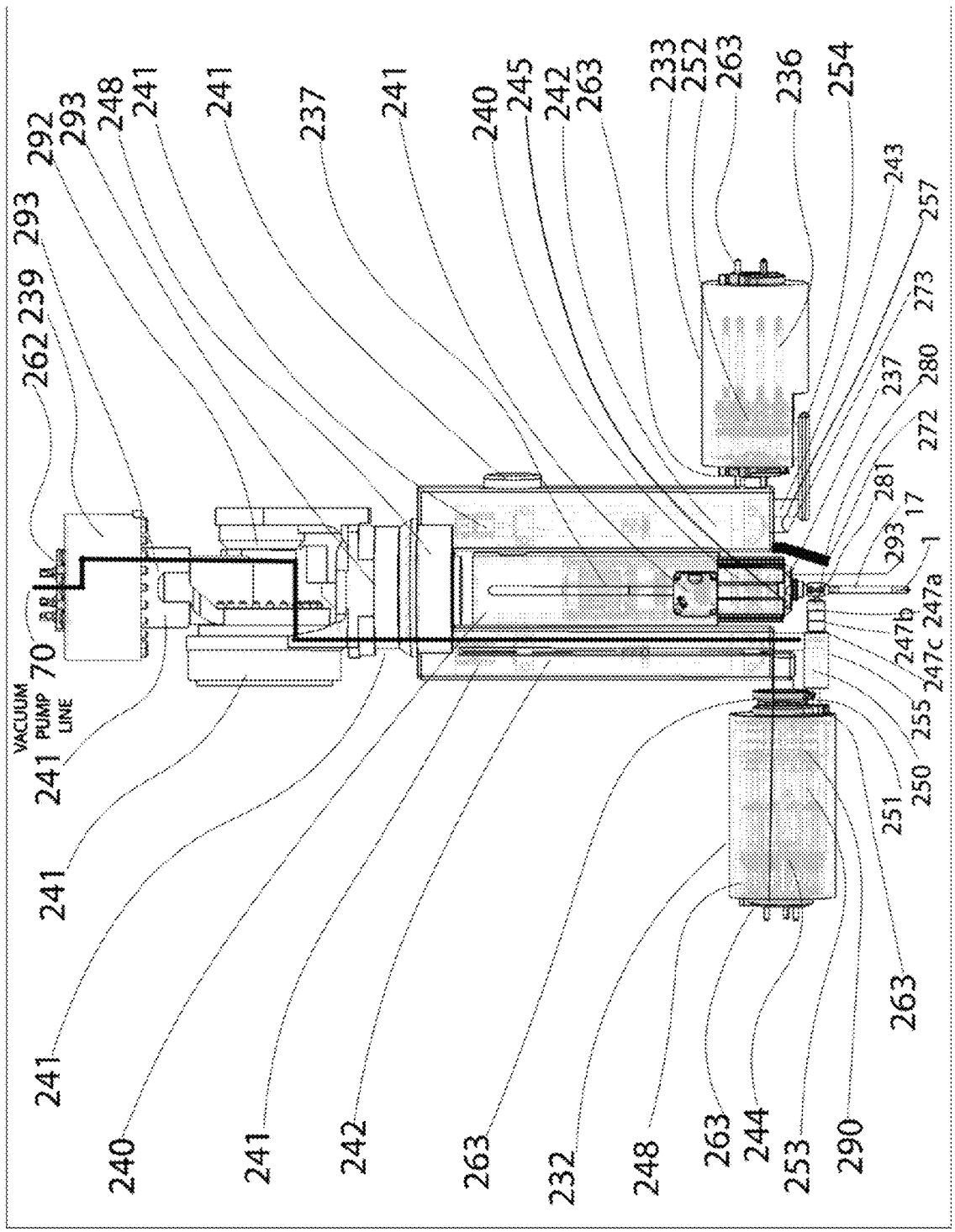
FIG. 13 is a schematic illustration of a front view of TruProid® sampling & profiling head-on sampling robot using a 19 mm hollow tungsten carbide vacuumed metal sampling head in accordance with the present disclosure.

An alternative second embodiment of the invention is disclosed as an automated detachable sampling head 239, TruProid® for nuclear-activated metal sampling and retrieval from within a radioactive waste handling hot cell 520 of large highly activated and radioactive metal components 270 removed from the nuclear reactor core is shown in FIGS. 12 and 13. A description of those identical parts or those described in connection with the embodiment is illustrated in FIGS. 1, 2, and 3 will not be repeated here. The metal sampling and activation profiling invention cuts, retrieves, and collects an incremental representative filings and chippings metal sample from the activated metal component sequentially providing an activation and tritium profile at depth from the easily measured surface with tritium contamination or acquire a "clean" metal sample from the bottom increment of the hole profiled. This bit allows confident metal sampling and retrieval and quantitatively analysis for upfront volumetric activation and radiochemical characterization data concerning tritium and activation products. It also allows the strict control of the tritium inventory of the large, activated component waste stream by maximizing the total tritium recovery from the reactor process components by accounting for tritium at depth. Thus, proving the tritium decontamination furnaces have entirely driven off all bound tritium, thus providing defensible data that the Waste Acceptance Criteria concerning tritium has been met, decreasing the radioactive waste characterization uncertainties. The TruProid® sampling unit, a 3-axis autonomous sampling and profiling head in conjunction with the massive reach of a 6-axis robot, survives the high radiation fields and remote handling constraints of sample transfer through transfer tunnels radiochemistry lab analytical operations area.

TABLE 4

Summary of Reactor Bioshield Material Volumes and Masses with Estimated Summation of Activities of Major Radionuclides of Concern Based Upon Hole 1

| Material | Ilmulate Concrete Radial Walls, Axial Walls, Floor & Ceiling 24 cm thick | | Mild Steel Vault Liner | | Aluminum Calandria Outer with Stiffening Ribs and End Plates Only 12.7 mm thick | |
|---|---|---|---|---|---|---|
| Density g/cm$^3$ | 3.692 | | 7.85 | | 2.68 | |
| Volume cm$^3$ | 1.19E+08 | | 2.21E+06 | | 2.62E+03 | |
| Mass Tons | 439.00 | | 17.30 | | 7.02 | |
| Activation Products | Bq/g | Total Bq | Bq/g | Bq/g | Total Bq | Bq/g |
| H-3 | 3.22E+03 | 1.41E+12 | 1.36E+01 | 1.02E+04 | 4.61E+09 | 7.03E+03 |
| C-14 | 5.49E+01 | 2.40E+10 | 4.70E+00 | 5.87E+01 | 2.65E+07 | 4.28E+02 |
| CI-36 | 3.97E-01 | 1.74E+08 | 6.31E-01 | 5.74E+00 | 2.59E+06 | 8.45E+00 |
| Ca-41/45 | 1 74E+01 | 7.62E+09 | NA | NA | NA | NA |
| Fe-55 | 1.79E+02 | 7.84E+10 | 1.00E+03 | 6.61E+03 | 2.99E+09 | 3.39E+04 |
| Ni-63 | 1.56E+02 | 6.83E+10 | 2.54E+02 | 8.86E+04 | 4.00E+10 | 1.90E+05 |
| Ni-59 | <MDA | <MDA | <MDA | 7.18E+02 | 3.25E+08 | 8.69E+02 |
| Co-60 | 7.27E+02 | 3.18E+11 | 6.79E+02 | 1.61E+04 | 7.28E+09 | 5.67E+04 |
| Nb-94 | <MDA | <MDA | <MDA | <MDA | <MDA | <MDA |
| Eu-152/154/155 | 2.80E+02 | 1.23E+11 | 3.42E+00 | 4.49E+02 | 2.03E+08 | <MDA |
| Zr-93 | NA | NA | NA | NA | NA | NA |
| TOTAL | 4.63E+03 | 2.03E+12 | 1.96E+03 | 1.23E+05 | 5.55E+10 | 2.89E+05 |
| Fission Products & Actinides | Bq/g | Total Bq | Bq/g | Bq/g | Total Bq | Bq/g |
| Cs-137 | <MDA | <MDA | <MDA | 1.15E+03 | 5.20E+08 | 1.06E+04 |
| Sr-90 | NA | NA | 1.68E-01 | 7.77E+02 | 3.51E+08 | 4.58E+03 |
| Tc-99 | NA | NA | <MDA | <MDA | <MDA | <MDA |
| Pu-238 | 1.89E+00 | 8.30E+08 | MDA | 2.07E+01 | 9.36E+06 | 1.33E+02 |
| Pu-239/240 | 4.69E-02 | 2.06E+07 | MDA | 2.75E+01 | 1.24E+07 | 8.62E+01 |
| Pu-241 | NA | NA | NA | NA | NA | NA |
| U-235 | <MDA | <MDA | <MDA | <MDA | <MDA | <MDA |
| U-238 | <MDA | <MDA | <MDA | <MDA | <MDA | <MDA |
| Sb-125 | <MDA | <MDA | <MDA | <MDA | <MDA | <MDA |
| Am-241 | <MDA | <MDA | <MDA | <MDA | <MDA | <MDA |
| TOTAL | 1.94E+00 | 8.50E+08 | 1.68E-01 | 1.98E+03 | 8.93E+08 | 1.54E+04 |
| GRAND TOTAL | 4.64E+03 | 2.04E+12 | 1.96E+03 | 1.25E+05 | 5.64E+10 | 3.04E+05 |

TABLE 4-continued

Summary of Reactor Bioshield Material Volumes and Masses with Estimated Summation of Activities of Major Radionuclides of Concern Based Upon Hole 1

| Material | Aluminum Calandria Inner Only 7 mm Thick | | Calandria Aluminum Tubes | | Zircaloy 2 Pressure Tubes | |
|---|---|---|---|---|---|---|
| Density g/cm$^3$ | 2.68 | | 2.68 | | 6.44 | |
| Volume cm$^3$ | 1.69E+05 | | 1.71E+03 | | 4.55E+03 | |
| Mass Tons | 0.452 | | 0.603 | | 3.87 | |
| Activation Products | Total Bq | Bq/g | Total Bq | Total Bq | Bq/g | Total Bq |
| H-3 | 4.24E+09 | 5.46E+04 | 2.11E+11 | 2.35E+08 | 3.96E+01 | 2.78E+08 |
| C-14 | 2.58E+08 | 1.37E+04 | 5.30E+10 | 8.13E+07 | 1.76E+00 | 1.24E+07 |
| CI-36 | 5.10E+06 | 8.86E+00 | 3.43E+07 | 1.09E+07 | 6.22E-01 | 4.37E+06 |
| Ca-41/45 | NA | NA | NA | NA | NA | NA |
| Fe-55 | 2.04E+10 | 4.62E+04 | 1.79E+11 | 1.73E+10 | 5.96E+00 | 4.18E+07 |
| Ni-63 | 1.15E+11 | 1.79E+06 | 6.93E+12 | 4.39E+09 | 3.14E+01 | 2.20E+08 |
| Ni-59 | 5.24E+08 | NA | NA | <MDA | <MDA | <MDA |
| Co-60 | 3.42E+10 | 7.21E+04 | 2.79E+11 | 1.17E+10 | 1.75E+01 | 1.23E+08 |
| Nb-94 | <MDA | 4.78E+01 | 1.85E+08 | <MDA | <MDA | <MDA |
| Eu-152/154/155 | <MDA | 9.00E+02 | 3.48E+09 | 5.92E+07 | 1.04E+01 | 7.30E+07 |
| Zr-93 | NA | 7.50.E+03 | 2.90E+10 | NA | NA | NA |
| TOTAL | 1.74E+11 | 1.99E+06 | 7.68E+12 | 3.38E+10 | 1.07E+02 | 7.53E+08 |
| Fission Products & Actinides | Total Bq | Bq/g | Total Bq | Total Bq | Bq/g | Total Bq |
| Cs-137 | 6.39E+09 | 1.57E+04 | 6.08E+10 | <MDA | 6.18E-01 | 4.34E+06 |
| Sr-90 | 2.76E+09 | 6.00E+03 | 2.32E+10 | 2.91E+06 | 5.54E-01 | 3.89E+06 |
| Tc-99 | <MDA | NA | NA | <MDA | <MDA | <MDA |
| Pu-238 | 8.02E+07 | 1.62E+02 | 6.27E+08 | MDA | MDA | MDA |
| Pu-239/240 | 5.20E+07 | 1.09E+02 | 4.22E+08 | MDA | MDA | MDA |
| Pu-241 | NA | 2.08E+03 | 8.05E+09 | NA | NA | NA |
| U-235 | <MDA | 4.00E-04 | 1.55E+03 | <MDA | <MDA | <MDA |
| U-238 | <MDA | 2.00E-02 | 7.74E+04 | <MDA | 1.73E-02 | 1.21E+05 |
| Sb-125 | <MDA | 6.96E+03 | 2.69E+10 | <MDA | <MDA | <MDA |
| Am-241 | <MDA | 3.32E+02 | 1.28E+09 | <MDA | <MDA | <MDA |
| TOTAL | 9.29E+09 | 3.13E+04 | 1.21E+11 | 2.91E+06 | 1.19E+00 | 8.35E+06 |
| GRAND TOTAL | 1.84E+11 | 2.02E+06 | 7.80E+12 | 3.38E+10 | 1.08E+02 | 7.61E+08 |

Although the present invention has been described in conjunction with preferred embodiments, it is to be understood that modifications and variations may be resorted to without departing from the spirit and scope of the invention, as those skilled in the art will readily understand. The use of the invention in this embodiment necessitates, as shown in FIGS. 8a, 8b, 9, and 10, with side views of the 19 mm hollow tungsten carbide vacuumed metal sampling head in accordance with the present disclosure, a hollow tungsten carbide sampling head 1 to capture a single discrete and unique metal particulate sample and all fugitive tritium inside a replaceable cartridge body 36 or for multiple sample collection through the same sampling point entry hole in a rotating manifold of the rotating filter and tritium trap carousel 232 and drill bit carousel 233 to purge tritium and prevent cross-contamination of remotely retrieved samples of highly activated and tritium contaminated nuclear reactor large internal components 270. Due to the variation in specific drilling approaches to varying materials and depths of cut requirements, a robot solid base 300 with adjustable sample head drilling 239 and sample collection platform is used to achieve successfully and repeatedly representative dry samples with retrieval to the adjacent radiochemical laboratory, through a 1.3 m thick concrete containment wall from the interior of a red zone hot cell environment. The hot cell red zone environment of 500 Sieverts per hour or more conditions, like humidity and temperature and the highly elevated ambient tritium concentrations within a hot cell, causes a high possibility of cross-contamination between interfacing components and the metal alloy samples. Large metal components 270 mounted and fixed on large facility mobile pallets 290 will have multiple sample locations accessed, and robot arm locked off for sampling operations by the sampling head and profiling penetration through the easily measured component surface to depth and cut and retrieve metal samples from the activated components, transferring hermetically out of the hot cell to the adjacent radiochemical laboratory for radioanalysis.

The remotely operated robotic hot cell sampling machine 900 and the automated detachable sampling head system 248 is mounted on the end arm of the hot cell automated sampling machine robot 900. It uses the TruProBit hollow tungsten carbide metal sampling drill bit 1 to capture metal particulate and fugitive tritium within the drill tube body 17 of the hollow drill bit, and in hermetic seal via seal with a replaceable metal tubular cartridge 74 that collects and contains the activated metal filings and chip sample with retrieval and collection within the cartridge body 25 for single sample retrieval. For multiple incremental metal sample collection, as shown in FIG. 13. the front view of TruProid® sampling & profiling head-on sampling robot 900 using a 19 mm hollow tungsten carbide vacuumed metal sampling head in accordance with the present disclosure, and profiling from the surface to depth, through one single point entry hole without sample cross-contamination, and retrieval uses a rotating carousel manifold of clean drill bits 233 and a rotating carousel of clean filters, with clean tritium traps 232 and is purged with cold, clean nitrogen gas so hot cell background ambient tritium is purged from ever entering each of the sealed stainless steel sealed carousels. This tritium purge of the carousels negates the cross-contamination of the remotely retrieved samples of highly activated and tritium contaminated nuclear reactor internal metal and graphite components. The TruProBit® metal sampling and profiling process's sampling performance addresses the following critical aspects and points of hot cell sampling and characterization implementation. A heavy-duty rotary cutting drill 245 and metal cutting bit 1 is used to penetrate the extremely resistant and hard activated metal alloy materials dry to produce incremental filings and chippings of samples. The activated metal radwaste sampling machine in the present embodiment of the invention may be a metal pallet 300 mounted robot 900 with a waste profiling sampling head unit system 248 that allows for sampling remotely and autonomously from within a hot cell with a high dose field of 500 Sieverts per hour. For instance, the profiling unit 248 may contain a radiation-hardened drill press motor coupling 240 for a TruProid® drill bit sampling head 1, a TruProBit® drill bit carousel 233, and a filter carousel 232.

Drilling and sampling highly activated metal stainless steel, tungsten, and alloy steel material within a hot cell using a 4.6 m reach robot 900 in conjunction with a TruProid® sampling head is totally contained. The functional design of the automated 3 axis sampling head attached to the 6-axis robot as shown in FIGS. 12 and 13 is the best viable approach and working envelope for such extreme radiation environments with sampling and characterization allowing access and be able to penetrate all drilling angles required to collect deep metal samples of the activated large hard metal components reliably, repeatedly, representatively and avoid all cross-contamination between incremental samples and collect all fugitive tritium for each respective unique sample.

The drilling head 239, sample filter 233, and drill bit 232 unit carousel is attached to the robot 900 using a robotic connector module 262, 263, respectively. A large load connecting module 262 is used to connect the sampling head to the robot, and 263 paired medium load connecting modules for the 30 cm diameter ends of the filter and drill bit carousels. The connector modules ensure a robust and reliable connection of the robot plate with the tool plate in a locked position, with zero backlash, which is paramount during the sampling operation and sample transfer process. The sampling head system comprises a mini gantry press assembly 240 for in and out drill bit placement, with a large metal cutting drill 245 to turn and drive the TruProBit® to cut and sample and retrieve metal samples. The drill bit automatic changer 252 with nine replaceable drill tips 236 in a carousel 233 is coupled to a spindle 237 with 3 HP electric motor with variable speed control. The filter automatic changer 253 with ten sample filters 244 in a carousel 232 rotates into position and with a push/pull filter actuator to interface with the drill bit. A new drill bit carousel 233 with 9 new clean sampling head drill bits 236 and a new filter carousel 232 with 10 new sample filter units 244 and tritium trap units are attached to a gimble head, all enclosed within the carousel stainless steel dust cover to prevent cross-contamination. The particulate filter system and tritium trap manifold filters rotate into position, and the push/pull filter actuator to interface the sample collection filter with the drill detachable sampling head 239. The new clean drill bit 236 lowers from horizontal to a vertical position, and the automatic drill bit changer arm 254 keys into the ISO40 tool holder body 255 securely. A new drill bit 236 is used for each activated component selected sampling location. The drill bit 236 is switched out once the depth of 1 mm is drilled through and profiled. The perpendicular drilling movement to the material surface being sampled is achieved by locking off the robot arm statistic and the use of a mini gantry drill press assembly 240 spindle and spindle motor which allows straight into hole concentric movement into the sampled material so no hot activated upper materials mix with cleaner material lower layer or the non-activated deeper material depth increments. All torsional drilling forces are contained in the sampling head machine 248 and a robotic arm to negate any risk of assembly movement as the drill bit rotates, and the sample is retrieved at the expected depths for incremental sample depths. The drill bit 236 lowers down to clear the bottom of the drill bit carousel 233 by the mechanical drill bit changer arm 254 moving forward using a stepper motor 241 and ball screw thread mechanism 242 for precise positioning using an actuator 243. The mechanical drill bit changer arm 254 moving through 180 degrees brings the drill bit and tool holder 255 into concentric alignment with the spindle quick-connect point. The whole drill bit and adapter, and tool holder is moved 180 degrees as one unit. Once aligned, it is then retracted into the automatic lock off in the spindle head. The automatic tool change arm 254 in the same motion aligns the sample filter unit connection point. The vacuum adaptors 250 are used to connect the drill bit to the sample filter unit with the connector kit 251 to connect the sample filter unit to the vacuum line inside the drill bit holder 252. A new clean sample filter unit 244 is pushed by a stepper motor driven actuator plunger pushing the new sample filter unit 244 onto the drill bit adapter connection point snuggly and held into position at the back of the drill bit by the filter unit changeout arm aligning concentrically. Once the sampling head 1 is brought into position above the sampling location entry point on the metal component surface 270, the mini gantry drill press 240 is moved forward slowly by use of stepper motor 241 and rotated slowly to move the sampling head and carefully lowered smoothly into close proximity to the surface to be sampled. This operation may be viewed by the video camera 273. A new clean sample filter unit 244 is in position, and the stepper motor driven actuator plunger retracts back into the carousel. The drill motor drives the spindle 237, which turns the drill bit and moves forward 1 mm using the drill press stepper motor drive mechanism 240, so the drill bit cuts and retrieves a metal sample into the filter unit. The drill motor stops, and the sample filter unit is retracted with the collected sample back into the filter carousel in its own unique sample retrieval chamber to avoid cross-contamination between consecutive sample increments. The filter carousel 232 rotates using an internal stepper motor rotated precisely into position, and the next clean sample filter unit chamber is aligned with the sample filter changeout alignment arm 254. A new filter 244 is pushed onto the drill bit adapter connection. The next increment sample is sampled and collected. During the sample collection, the drill bit rotates, and the air suction collects the dust and tritium in the first filter shown in FIG. 13. Once the drill bit stops rotating, the carousel rotates to the next filter. Continue drilling until the drill bit is to be changed, or all carousel filters are used. A purge nitrogen gas at drill bit carousel and filter unit carousel is used to dissipate hot cell ambient tritium into sample intake and filter handling components. The filter unit's direct contact to the back end shank eliminates cross-contamination by reducing the contact surfaces to be constantly replaced. There is no connection tubing from drill to filter, so this eliminates the chances of cross-contamination, and so direct mating of the drill bit and the filter is the optimal configuration to eliminate the chance of any cross-contamination between activated metal samples.

Incorporated in the system is a spindle 237 for tool changing and to reduce drill motor wear and tear and an Infra-red camera 259 to observe any fire hazards and any heat source in an inaccessible high radiation zone-a laser positioning system with camera 273 for drill bit positioning and repositioning in the same hole. A high-pressure air blaster 272 is utilized to clean drill bit mating interfaces and clear any loose contamination of the camera lens or the tool holder interface.

The sample collection unit 263 is moved in and out of the carousel by an actuator 243, which may comprise a revolving series of 60 cm³, 0.01 um filter units 247a, 247b, and 247c, housed in a stainless-steel casing that can be unscrewed. The sample is captured in the first stage of the sample particulate filter unit 247a and charcoal traps, primary 247b, and secondary in series 247c to capture the fugitive tritium via a vacuum line 70. This is achieved using a flow of dry cold nitrogen air to draw and collect the metal sample debris with tritium traps collecting all the fugitive tritium during the particulate sample collection. The combined particulate tritium activity with the fugitive tritium trap activity gives the metal component's total tritium activity sampled. Silica gel that changes color to blue if moisture penetrates through each of the inline fugitive tritium back traps are used to collect the tritiated water, HTO. Silica gel is an amorphous and porous form of silicon dioxide silica with a high specific surface area, which allows it to absorb water readily onto the surface. The charcoal traps 247b and 247c absorb the gaseous tritium. This ensures containment of dust and volatile tritium and organics before the air passes through the vacuum pump. The metal filings and chippings are retrieved for radioanalysis by dispensing the metal sample into a sealed clean pre-weighed sample pot before being weighed out for appropriate radiometric measurement. It is approx. $35,000/g of tritium as fuel; therefore, it is evident that recovering all the tritium from heating in hot cell furnaces is cost-effective.

The TruProid® Sampling Head 1, when locked off static on the heavy-lift robot arm, has an independent separate control system for delivery of the sampling head of the drill bit to the surface of the activated tritium contaminated metal waste component surface, mitigating the risk of crushing using a proximity sensor. It is a physical stop of all machine movement on instantaneous collision detection. The activated metal component sampling machine 248 may be sized such that it can span and access all waste surfaces to be sampled and profiled for tritium for the large metal component 270 mounted on a rotatable large metal palette 290 that is moved on rails 280 inside the hot cell, rotated into position for metal alloy sampling and profiling. The hot cell 520 may also comprise access ports, posting in port 320 and posting out port 310 through the post out port transfer tunnel 510 and the posting in port through hot cell wall 520 tunnel in port tunnel 530. The carousel of captured samples is posted out through port 310 through transfer tunnel 510, port 310 is closed before opening transfer port 330, and the sample filter carousel 232 is transferred into the lab receiving glovebox 380 through the lab transfer automated posting out port 370 using a lightweight lab transfer robot 400. The sample carousel is decontaminated and transferred via glovebox post 350 through transfer tunnel 360 into lab transfer glovebox 390, whereupon the sample filter carousel 232 is opened, and the collected sample filters and tritium field blank removed and transferred to the radiological laboratory through port 340 for activation radioanalysis of the collected metal chip and metal filing samples. The new clean filter carousel 232 and drill bit carousel 233 is posted through port 310 through transfer tunnel 530, port 310 is closed before opening transfer port 320, and the new clean sample filter carousel 232 is transferred into the hot cell from the lab receiving glovebox 390 using a lightweight lab transfer robot 400. The new sample and drill bit carousels are transferred via glovebox port 320 into the hot cell 520 via the carousel quick-connect connectors 263 on the sampling head. Whereupon the sampling at a new sampling location can commence, confident no cross-contamination between samples occurs. TruProid® automated sampling head 239 with independently operated sampling mini drill press 240 may orientate a drill bit 1 in and out of the sampling point location on then activated metal component 270. The 6-axis robot arm control system controls the in-cell robot motors. These features enable integrating the motor control functions with TruProid® sampling head 248 and sampling system operations. The vacuum pump 234 will run continuously as the drill bit cuts the material, totally collecting and completely capturing all metal filings and chippings of material, and fugitive tritium evolved from the sampling operation. The sampling station area lighting has sixteen LED lamps ceiling mounted for lighting with hot cell room cameras 249, to observe sampling and sample collection operations. Three 5.5 mm HD cameras 257 are used to observe the drilling operation, and an 8 mm, CZT gamma probe, is shielded with a lead collimator to measure the dose rate before transferring out of the cell. Drilling technique through such hard and "hot" materials "dry" is paramount. Although the present invention has been described in conjunction with preferred embodiments, it is to be understood that modifications and variations may be resorted to without departing from the spirit and scope of the invention, as those skilled in the art will readily understand. The above-described embodiments illustrate only a few of the possible specific embodiments that can represent the invention's applications. Numerous and varied other arrangements can be made by those skilled in the art without departing from the spirit and scope of the activated core components metal sampling and characterization tool invention.

The invention claimed is:

1. A method which includes collecting nuclear reactor core samples in-situ
   from one or more layers of irradiated core material by using a metal-cutting drill bit made of tungsten carbide, the method comprising:
   penetrating an outer concrete bioshield wall of the nuclear reactor using a masonry drill bit;
   after penetrating the outer concrete bioshield wall, replacing the masonry drill bit with the metal-cutting drill bit, wherein the metal-cutting drill bit includes:
   a hollow drill bit shaft body, having an interior airflow passage formed therein, sitting concentrically along a longitudinal axis of the metal-cutting drill bit;
   a tungsten carbide sampling cutting head with
   a plurality of cutting arms extending radially outward with equally spaced chip grooves along a cutting face of the tungsten carbide sampling cutting head
   and a plurality of air holes formed through a flank face of the tungsten carbide sampling cutting head, in communication with the airflow passage, wherein the plurality of cutting arms are spaced apart radially about a central axis of the tungsten carbide sampling cutting head; and
   at least one particulate air guide behind the plurality of cutting arms operable to guide air and particulate forward to behind the tungsten carbide sampling cutting head;

taking an incremental sample at a predetermined increment by rotationally cutting into a metal alloy object or metal component of the core to produce one or more of metal chips, filings, and dust; and collecting the one or more of metal chips, filings, and dust within a filter which is located within a hermetically sealed containment glove box in hermetic communication with the airflow passage, wherein said collecting is performed by creating a vacuumed airflow through the airflow passage and at the tungsten carbide sampling cutting head causing the one or more of metal chips, filings, and dust to be pulled through the plurality of air holes and into the airflow passage and ultimately into the filter.

2. The method of claim 1, further comprising determining insitu a level of radioactivity within the one or more of metal chips, filings, and dust of the incremental sample by analyzing the one or more of metal chips, filings, and dust of the incremental sample.

3. The method of claim 2, wherein said determining comprises determining an amount of one or more of
nuclear irradiated products,
tritium, and
ruptured nuclear fuel element fission product contaminants
in the incremental sample.

4. The method of claim 2, wherein a total time from taking the incremental sample to completion of analysis of the one or more of metal chips, filings, and dust of the incremental sample is 15 minutes or less.

5. The method of claim 2, wherein said analyzing comprises using Alpha Beta Gamma radioanalysis.

6. The method of claim 2, further comprising:
replacing the filter with a new filter, and
repeating said rotationally cutting and said collecting for a subsequent incremental sample.

7. The method of claim 6, further comprising determining insitu a level of radioactivity within the one or more of metal chips, filings, and dust of the subsequent incremental sample by analyzing the one or more of metal chips, filings, and dust of the subsequent incremental sample.

8. The method of claim 6, further comprising
producing actual irradiated product characterization data based
at least in part on
the level of radioactivity within the incremental sample
and the level of radioactivity within the subsequent incremental sample.

9. The method of claim 8, further comprising using the actual irradiated product characterization data as part of a site nuclear power plant decommissioning plan.

10. The method of claim 7, wherein a total time from taking the subsequent incremental sample to completion of analysis of the one or more of metal chips, filings, and dust of the subsequent incremental sample is 15 minutes or less.

11. The method of claim 1, wherein the predetermined increment comprises a 1-millimeter increment.

12. The method of claim 1, wherein said rotationally cutting is performed without use of any of water, oils, and lubricants.

13. The method of claim 1, wherein the irradiated core material comprises an internal lateral screen of the nuclear reactor.

14. The method of claim 1, wherein the irradiated core material comprises
an inner stainless steel vessel shell ring of the nuclear reactor
or a Zircaloy pressure tube of the nuclear reactor.

15. The method of claim 1, wherein the nuclear reactor comprises a nuclear fission reactor or a nuclear fusion reactor.

16. The method of claim 1, wherein the method is performed as part of or in support of a decommissioning strategy relating to the nuclear reactor.

17. The method of claim 1, wherein the plurality of cutting arms includes a first cutting arm having two of the chip grooves and a second cutting arm having three of the chip grooves.

18. The method of claim 1, further comprising during said taking or said collecting, dislodging blocked or backed up metal chips, filings, or dust sampling debris
by causing
a shank
and a drill tube body to which the metal-cutting drill bit is coupled
and the metal-cutting drill bit
to vibrate.

19. The method of claim 1, wherein said collecting is performed during said taking and wherein the method further comprises air-cooling the tungsten carbide sampling cutting head by continuously providing the vacuumed airflow.

20. The method of claim 1, further comprising, prior to penetrating the outer concrete bioshield wall:
supporting drilling to 1,651 inches deep by anchoring a sampling gantry to the outer concrete bioshield wall; and
establishing a sampling angle of declination of the sampling gantry to between 0 and 30 degrees; and
presenting the masonry drill bit to a surface of the outer concrete bioshield wall.

* * * * *